(12) United States Patent
Strachan et al.

(10) Patent No.: US 9,563,743 B2
(45) Date of Patent: Feb. 7, 2017

(54) ANALYTE TESTING METHOD AND SYSTEM WITH HIGH AND LOW BLOOD GLUCOSE TRENDS NOTIFICATION

(75) Inventors: Alexander Strachan, Moray (GB); David Price, Pleasanton, CA (US); Gillian Teft, Maryburgh (GB); Robert Cavaye, Penarth (GB); Miya Osaki, Brooklyn, NY (US); Kimberly Mingo Ventura, Brooklyn, NY (US); Lisa Powell, Minneapolis, MN (US); Kyia Downing, Shoreview, MN (US)

(73) Assignee: LifeScan Scotland Limited, Inverness (GB)

( * ) Notice: Subject to any disclaimer, the term of this patent is extended or adjusted under 35 U.S.C. 154(b) by 856 days.

(21) Appl. No.: 12/826,543

(22) Filed: Jun. 29, 2010

(65) Prior Publication Data

US 2011/0205064 A1 Aug. 25, 2011

Related U.S. Application Data

(60) Provisional application No. 61/308,217, filed on Feb. 25, 2010, provisional application No. 61/322,697, filed on Apr. 9, 2010.

(51) Int. Cl.
| | | |
|---|---|---|
| G08B 23/00 | (2006.01) | |
| G06F 19/00 | (2011.01) | |
| A61B 5/145 | (2006.01) | |
| A61B 5/00 | (2006.01) | |

(52) U.S. Cl.
CPC ....... *G06F 19/3406* (2013.01); *A61B 5/14532* (2013.01); *A61B 5/7275* (2013.01); *G06F 19/345* (2013.01); *G06F 19/3443* (2013.01)

(58) Field of Classification Search
CPC .............. A61B 5/14532; A61B 5/7275; A61M 5/1723; A61M 2230/201; C12Q 1/54; G08B 21/24; G08B 21/245; G06F 19/3406; G06F 19/345; G06F 19/3443
USPC ......... 340/573.1, 539.12, 540; 600/316, 347, 600/365; 604/504; 435/14
See application file for complete search history.

(56) References Cited

U.S. PATENT DOCUMENTS

| | | | |
|---|---|---|---|
| 4,731,726 | A | 3/1988 | Allen |
| 5,251,126 | A | 10/1993 | Kahn et al. |
| 5,822,715 | A | 10/1998 | Worthington et al. |
| 6,179,979 | B1 | 1/2001 | Hodges et al. |
| 6,193,873 | B1 | 2/2001 | Ohara et al. |
| 6,280,409 | B1 | 8/2001 | Stone et al. |
| 6,284,125 | B1 | 9/2001 | Hodges et al. |
| 6,309,884 | B1 | 10/2001 | Cooper et al. |

(Continued)

FOREIGN PATENT DOCUMENTS

| | | |
|---|---|---|
| EP | 0483595 | 12/2001 |
| EP | 1338295 A1 | 8/2003 |

(Continued)

OTHER PUBLICATIONS

International Search Report, PCT Application No. PCT/US2010/040425, Dated Dec. 23, 2010, 7 pages, European Patent Office, Rijswijk, Netherlands.

(Continued)

*Primary Examiner* — An T Nguyen

(57) ABSTRACT

Described herein are systems and methods to utilize factual information based on stored blood glucose data to allow greater insight into the management of diabetes of a user.

16 Claims, 16 Drawing Sheets

(56) References Cited

U.S. PATENT DOCUMENTS

| | | | |
|---|---|---|---|
| 6,379,301 B1 | 4/2002 | Worthington et al. |
| 6,413,410 B1 | 7/2002 | Hodges et al. |
| 6,425,863 B1 | 7/2002 | Werner et al. |
| 6,475,372 B1 | 11/2002 | Ohara et al. |
| 6,544,212 B2 | 4/2003 | Galley et al. |
| 6,558,351 B1 | 5/2003 | Steil et al. |
| 6,572,542 B1 | 6/2003 | Houben et al. |
| 6,633,772 B2 | 10/2003 | Ford et al. |
| 6,635,167 B1 | 10/2003 | Batman et al. |
| 6,656,114 B1 | 12/2003 | Poulsen et al. |
| 6,691,043 B2 | 2/2004 | Ribeiro, Jr. et al. |
| 6,716,577 B1 | 4/2004 | Yu et al. |
| 6,749,887 B1 | 6/2004 | Dick et al. |
| 6,862,466 B2 | 3/2005 | Ackerman |
| 6,863,801 B2 | 3/2005 | Hodges et al. |
| 6,890,421 B2 | 5/2005 | Ohara et al. |
| 6,941,163 B2 | 9/2005 | Ford et al. |
| 7,022,072 B2 | 4/2006 | Fox et al. |
| 7,024,236 B2 | 4/2006 | Ford et al. |
| 7,045,046 B2 | 5/2006 | Chambers et al. |
| 7,060,059 B2 | 6/2006 | Keith et al. |
| 7,179,226 B2 | 2/2007 | Crothall et al. |
| 7,204,823 B2 | 4/2007 | Estes et al. |
| 7,241,265 B2 * | 7/2007 | Cummings ........ A61B 5/7475 128/920 |
| 7,267,665 B2 | 9/2007 | Steil et al. |
| 7,282,029 B1 | 10/2007 | Poulsen et al. |
| 7,291,107 B2 | 11/2007 | Hellwig et al. |
| 7,291,256 B2 | 11/2007 | Teodorczyk et al. |
| 7,354,420 B2 | 4/2008 | Steil et al. |
| 7,399,277 B2 | 7/2008 | Saidara et al. |
| 7,402,153 B2 | 7/2008 | Steil et al. |
| 7,404,796 B2 | 7/2008 | Ginsberg |
| 7,498,132 B2 | 3/2009 | Yu et al. |
| 7,509,156 B2 | 3/2009 | Flanders |
| 7,553,281 B2 | 6/2009 | Hellwig et al. |
| 7,651,489 B2 | 1/2010 | Estes et al. |
| 8,974,387 B2 * | 3/2015 | Shadforth ........ A61B 5/14532 600/300 |
| 2002/0019707 A1 | 2/2002 | Cohen et al. |
| 2002/0026111 A1 | 2/2002 | Ackerman |
| 2003/0108976 A1 | 6/2003 | Braig et al. |
| 2003/0175806 A1 | 9/2003 | Rule et al. |
| 2003/0208113 A1 | 11/2003 | Mault et al. |
| 2003/0211617 A1 | 11/2003 | Jones |
| 2003/0220814 A1 | 11/2003 | Gordon |
| 2004/0059201 A1 | 3/2004 | Ginsberg |
| 2005/0004439 A1 | 1/2005 | Shin et al. |
| 2005/0027182 A1 | 2/2005 | Siddiqui et al. |
| 2005/0038332 A1 | 2/2005 | Saidara et al. |
| 2005/0090726 A1 | 4/2005 | Ackerman |
| 2005/0096511 A1 | 5/2005 | Fox et al. |
| 2005/0096512 A1 | 5/2005 | Fox et al. |
| 2005/0113653 A1 | 5/2005 | Fox et al. |
| 2005/0143864 A1 | 6/2005 | Blomquist |
| 2005/0176153 A1 | 8/2005 | O'Hara et al. |
| 2005/0182358 A1 | 8/2005 | Veit et al. |
| 2005/0214892 A1 | 9/2005 | Kovatchev et al. |
| 2006/0025663 A1 | 2/2006 | Talbot et al. |
| 2007/0010950 A1 | 1/2007 | Abensour et al. |
| 2007/0016127 A1 | 1/2007 | Staib et al. |
| 2007/0016449 A1 | 1/2007 | Cohen et al. |
| 2007/0060803 A1 | 3/2007 | Liljeryd et al. |
| 2007/0060813 A1 | 3/2007 | Chang |
| 2007/0083335 A1 | 4/2007 | Moerman et al. |
| 2007/0118589 A1 | 5/2007 | Brown |
| 2007/0173761 A1 | 7/2007 | Kanderiab, Jr. et al. |
| 2007/0208246 A1 | 9/2007 | Brauker et al. |
| 2007/0231914 A1 | 10/2007 | Deng et al. |
| 2007/0232880 A1 | 10/2007 | Siddiqui et al. |
| 2007/0276197 A1 | 11/2007 | Harmon |
| 2007/0287985 A1 | 12/2007 | Estes et al. |
| 2008/0045819 A1 | 2/2008 | Emoto et al. |
| 2008/0045825 A1 | 2/2008 | Melker et al. |
| 2008/0052057 A1 | 2/2008 | Brown |
| 2008/0097289 A1 | 4/2008 | Steil et al. |
| 2008/0119702 A1 | 5/2008 | Reggiardo et al. |
| 2008/0119710 A1 | 5/2008 | Reggiardo et al. |
| 2008/0125636 A1 | 5/2008 | Ward et al. |
| 2008/0139910 A1 | 6/2008 | Mastrototaro et al. |
| 2008/0154513 A1 | 6/2008 | Kovatchev et al. |
| 2008/0171967 A1 | 7/2008 | Bloomquist |
| 2008/0172027 A1 | 7/2008 | Bloomquist |
| 2008/0172028 A1 | 7/2008 | Bloomquist |
| 2008/0172029 A1 | 7/2008 | Bloomquist |
| 2008/0172031 A1 | 7/2008 | Bloomquist |
| 2008/0177154 A1 | 7/2008 | Hansen et al. |
| 2008/0183060 A1 | 7/2008 | Steil et al. |
| 2008/0187943 A1 | 8/2008 | Buse et al. |
| 2008/0188796 A1 | 8/2008 | Steil et al. |
| 2008/0199465 A1 | 8/2008 | Lake et al. |
| 2008/0206799 A1 | 8/2008 | Blomquist |
| 2008/0234943 A1 | 9/2008 | Ray et al. |
| 2008/0234992 A1 | 9/2008 | Ray et al. |
| 2008/0235053 A1 * | 9/2008 | Ray ................. G06Q 50/24 705/3 |
| 2008/0255438 A1 | 10/2008 | Saidara et al. |
| 2008/0262088 A1 | 10/2008 | Hauck et al. |
| 2008/0268485 A1 | 10/2008 | Guarino et al. |
| 2008/0269585 A1 | 10/2008 | Ginsberg |
| 2008/0294024 A1 | 11/2008 | Cosentino et al. |
| 2008/0312512 A1 | 12/2008 | Brukalo et al. |
| 2008/0312518 A1 | 12/2008 | Jina et al. |
| 2009/0006129 A1 | 1/2009 | Thukral et al. |
| 2009/0018495 A1 | 1/2009 | Panduro |
| 2009/0018779 A1 | 1/2009 | Cohen et al. |
| 2009/0030733 A1 | 1/2009 | Cohen et al. |
| 2009/0098587 A1 | 4/2009 | Hetzel et al. |
| 2009/0099506 A1 | 4/2009 | Estes et al. |
| 2009/0099509 A1 | 4/2009 | Estes et al. |
| 2009/0105570 A1 | 4/2009 | Sloan et al. |
| 2009/0112069 A1 | 4/2009 | Kanamori et al. |
| 2009/0112626 A1 | 4/2009 | Talbot et al. |
| 2009/0137455 A1 | 5/2009 | Steiner et al. |
| 2009/0149717 A1 | 6/2009 | Brauer et al. |
| 2009/0150186 A1 | 6/2009 | Cohen et al. |
| 2009/0156923 A1 | 6/2009 | Power et al. |
| 2009/0156924 A1 | 6/2009 | Shariati et al. |
| 2009/0177147 A1 | 7/2009 | Blomquist et al. |
| 2009/0184004 A1 | 7/2009 | Chatiler et al. |
| 2009/0237262 A1 | 9/2009 | Smith et al. |
| 2009/0240127 A1 | 9/2009 | Ray |
| 2009/0247982 A1 | 10/2009 | Krulevitch et al. |
| 2009/0292190 A1 | 11/2009 | Miyashita |
| 2010/0016700 A1 | 1/2010 | Sieh et al. |
| 2010/0041084 A1 | 2/2010 | Stephens et al. |
| 2010/0041960 A1 | 2/2010 | Yuan et al. |
| 2010/0174228 A1 | 7/2010 | Buckingham et al. |
| 2010/0331654 A1 * | 12/2010 | Jerdonek ........ A61B 5/14532 600/365 |
| 2011/0050428 A1 * | 3/2011 | Istoc ................. G06F 19/345 340/573.1 |
| 2011/0205064 A1 * | 8/2011 | Strachan ........ A61B 5/14532 340/573.1 |
| 2013/0318439 A1 * | 11/2013 | Landis ................. A61B 5/151 715/705 |

FOREIGN PATENT DOCUMENTS

| | | |
|---|---|---|
| EP | 1568310 A1 | 8/2005 |
| EP | 1677226 | 7/2006 |
| EP | 1770396 A2 | 4/2007 |
| EP | 1840219 A1 | 10/2007 |
| EP | 2455875 A2 | 5/2012 |
| JP | 2007317196 A | 12/2007 |
| JP | 2008501426 A | 1/2008 |
| JP | 2008508029 A | 3/2008 |
| JP | 2009037588 A | 2/2009 |
| WO | WO 98/37805 A1 | 9/1998 |
| WO | WO 02/00112 A2 | 1/2002 |
| WO | WO 03/030731 A2 | 4/2003 |
| WO | WO 03/045233 A1 | 6/2003 |
| WO | WO 2004/015539 A2 | 2/2004 |

(56) References Cited

FOREIGN PATENT DOCUMENTS

| WO | WO 2004/023972 A2 | 3/2004 |
|---|---|---|
| WO | WO 2005/093629 A2 | 10/2005 |
| WO | WO 2006/066038 | 6/2006 |
| WO | WO 2006/066583 A1 | 6/2006 |
| WO | WO 2006/133348 | 12/2006 |
| WO | WO 2007/005170 A2 | 1/2007 |
| WO | WO 2007/019289 | 2/2007 |
| WO | WO 2007/019384 | 2/2007 |
| WO | WO 2007/028271 | 3/2007 |
| WO | WO 2007/101260 | 9/2007 |
| WO | WO 2007/149533 | 12/2007 |
| WO | WO 2008/071218 | 6/2008 |
| WO | WO 2008/071444 | 6/2008 |
| WO | WO 2008/073609 A2 | 6/2008 |
| WO | WO 2008/094249 | 8/2008 |
| WO | WO 2009/005952 | 1/2009 |
| WO | WO 2009/005960 | 1/2009 |
| WO | WO 2009/016050 | 2/2009 |
| WO | WO 2009/137661 | 11/2009 |
| WO | 2011002791 A2 | 1/2011 |

OTHER PUBLICATIONS

Partial International Search Report, Annex to Form PCT/ISA/206, PCT Application No. PCT/US2010/040309, Dated Nov. 29, 2010, 2 pages, European Patent Office, Rijswijk, Netherlands.

International Search Report, PCT Application No. PCT/GB2010/001683, Dated Dec. 22, 2010, 4 pages, European Patent Office, Rijswijk, Netherlands.

Nathan, D.M., *Management of Hyperglycemia in Type 2 Diabetes: A Consensus Algorithm for the Initiation and Adjustment of Therapy*, Diabetes Care, vol. 29 No. 8, 1963-1972, Aug. 2006.

International PCT Patent Application No. PCT/US2010/040434, International Search Report, dated Oct. 20, 2010, 3 pgs, European Patent Office, Rijswijk.

International Search Report, PCT Application No. PCT/US2010/040383, dated Nov. 4, 2010, 3 pages, European Patent Office, Rijswijk.

William H. et al. *Numerical Recipes in C: The Art of Scientific Computing*. Cambridge: Cambridge University Press, 1992. ISBN 0-521-43108-5, pp. 226-230.

"Accu-Chek Complete Owner's Booklet", Roche Diagnostics, 2004, XP002636883, Retrieved from internet: URL:https://www.accu-chek.com/us/customer-care/downloads.html [retrieved May 12, 2011], p. 8, pp. 33-40, pp. 46 and 86.

International Search Report, PCT Application No. PCT/US2010/040443, dated May 17, 2011, 3 pages, European Patent Office, Rijswijk, NL.

European Application No. 10730658.1, European Office Action dated Aug. 20, 2013, 4 pages.

Patent Examination Report issued in related Australian Patent Application No. 2010346623, dated May 30, 2014, 3 pages.

European Search Report issued in related European Patent Application No. EP 13 15 1121, dated Apr. 10, 2013, 6 pages.

European Search Report issued in related European Patent Application No. Ep 13 15 1120, dated Apr. 10, 2013, 6 pages.

International Preliminary Report on Patentability issued in related International Application No. PCT/US2010/040434, May 31, 2012, 10 pages.

Notice of Reasons for Rejection issued in related Japanese Patent Application No. 2012-554979, dated Apr. 8, 2014, 4 pages.

Written Opinion issued in related International Application No. PCT/US2010/040434, Mar. 12, 2012, 6 pages.

Patent Examination Report issued in related Australian Application No. 2010346623, dated Jun. 4, 2015, 3 pages.

Notice of Preliminary Rejection issued in related Korean Patent Application No. 10-2012-7024554, mailed May 3, 2016, 15 pages.

Office Action issued in related Chinese Patent Application No. 201080064763.2, mailed Dec. 3, 2014, 17 pages. (Note: English translation will be provided upon request).

Notification on the Results of Patentability Check issued in related Russian Patent Application No. 2012140731, dated Jul. 7, 2014, 14 pages.

* cited by examiner

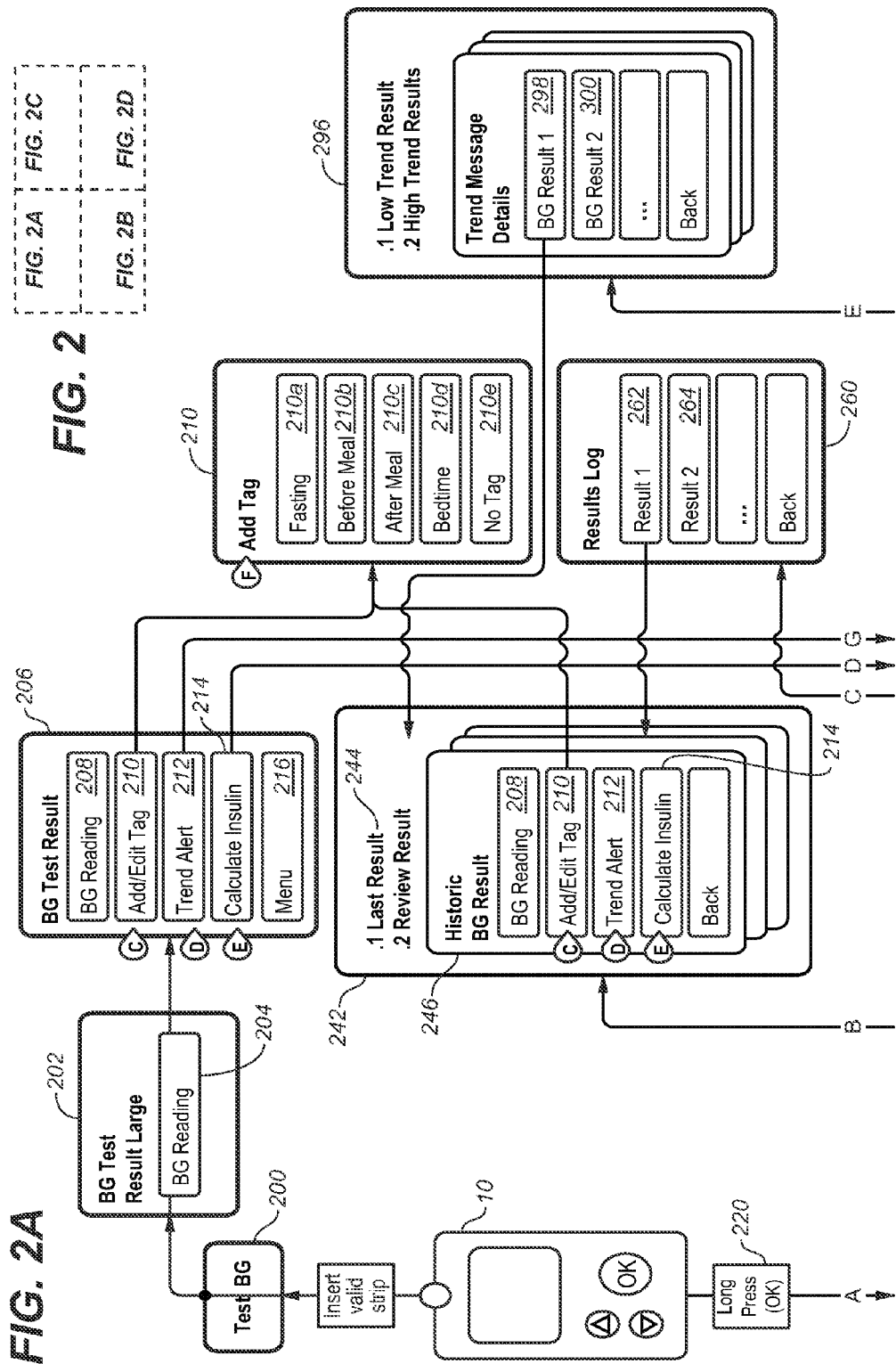

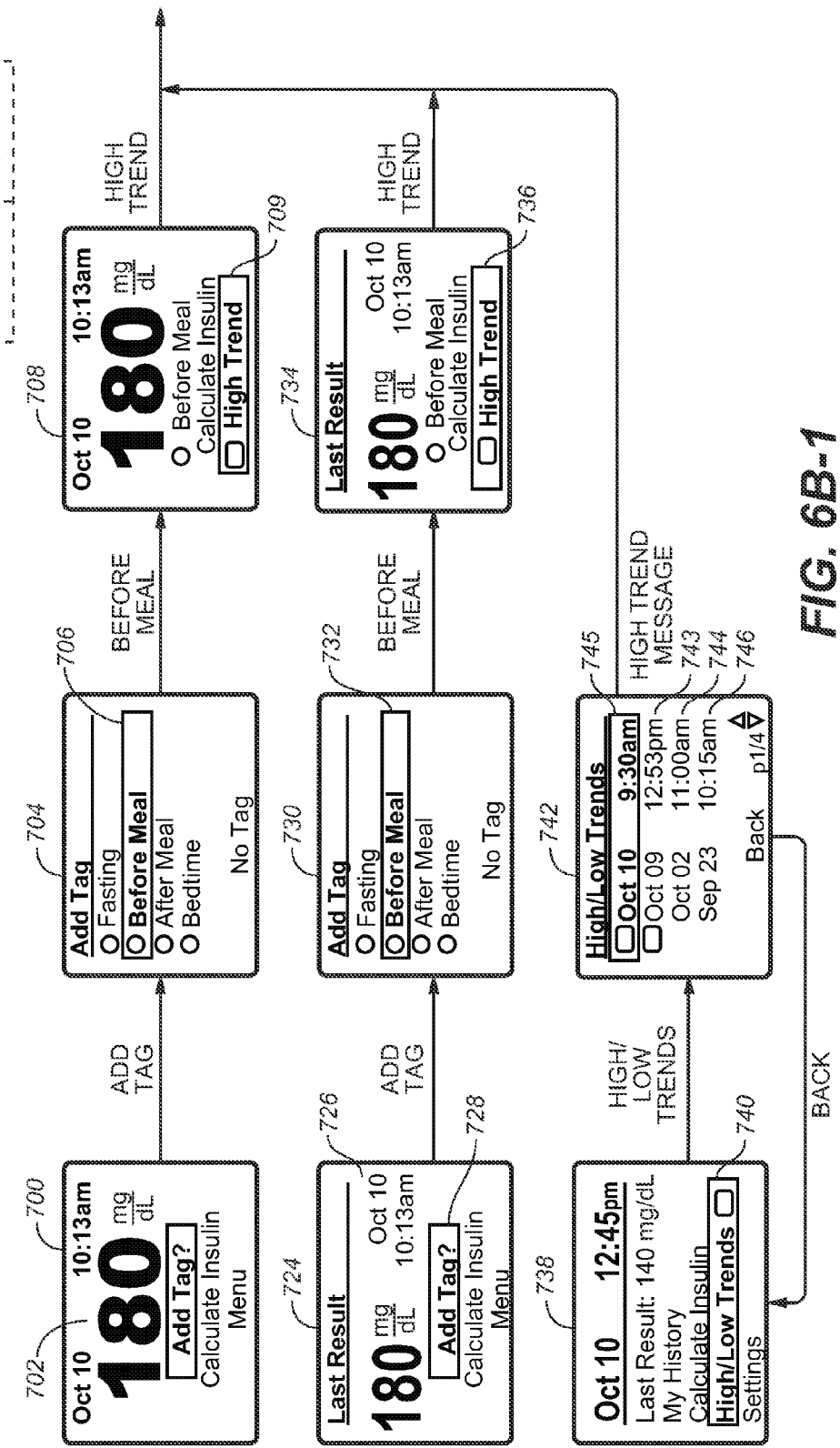

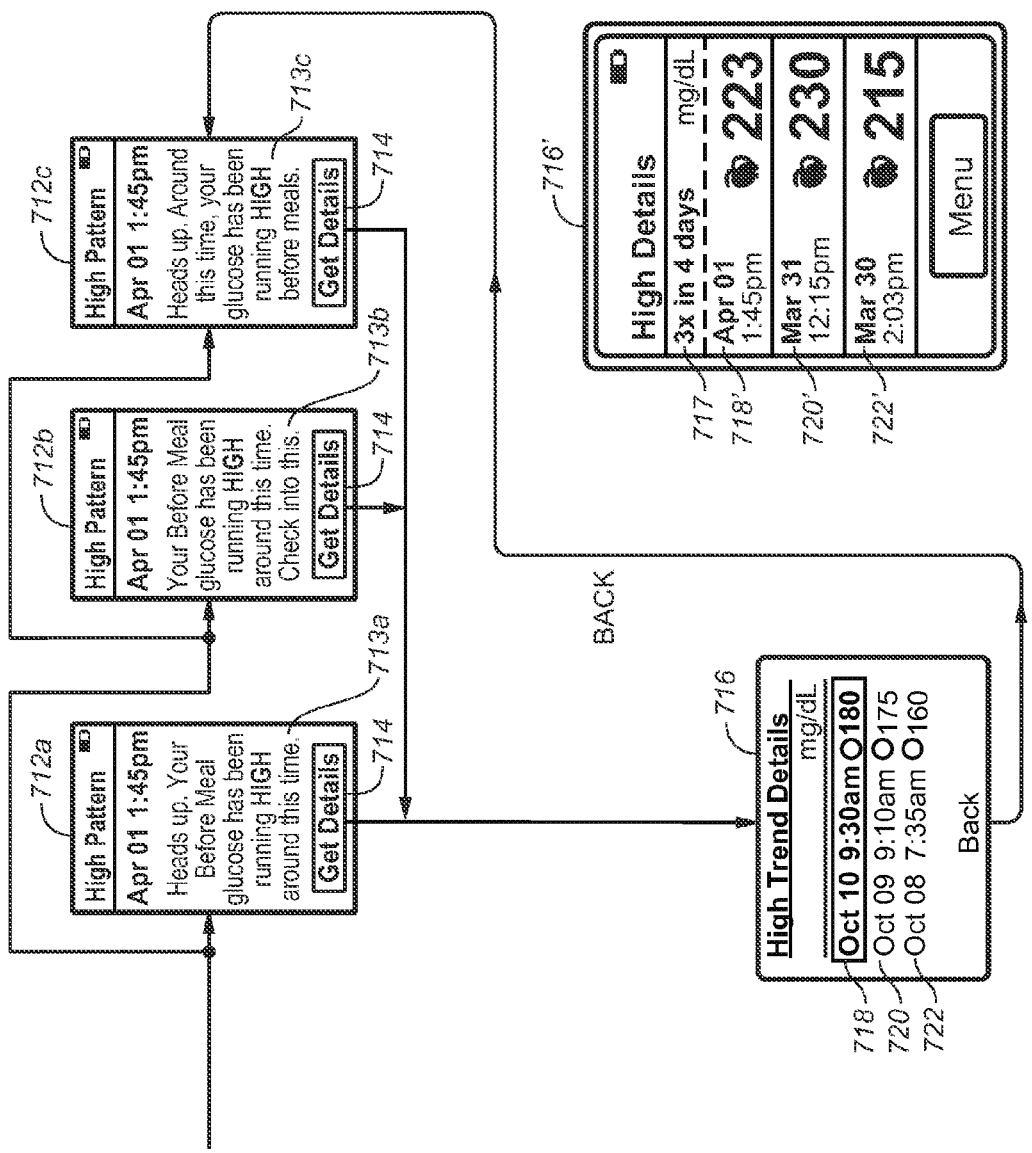

ANALYTE TESTING METHOD AND SYSTEM WITH HIGH AND LOW BLOOD GLUCOSE TRENDS NOTIFICATION

This application claims the benefits of priority under 35 USC§119 and/or §120 from prior filed U.S. Provisional Application Ser. Nos. 61/308,217 filed on Feb. 25, 2010, and 61/322,697 filed on Apr. 9, 2010, which applications are incorporated by reference in their entirety into this application.

BACKGROUND

Glucose monitoring is a fact of everyday life for diabetic individuals. The accuracy of such monitoring can significantly affect the health and ultimately the quality of life of the person with diabetes. Generally, a diabetic patient measures blood glucose levels several times a day to monitor and control blood sugar levels. Failure to test blood glucose levels accurately and on a regular basis can result in serious diabetes-related complications, including cardiovascular disease, kidney disease, nerve damage and blindness. There are a number of electronic devices currently available which enable an individual to test the glucose level in a small sample of blood. One such glucose meter is the OneTouch® Profile™ glucose meter, a product which is manufactured by LifeScan.

In addition to glucose monitoring, diabetic individuals often have to maintain tight control over their lifestyle, so that they are not adversely affected by, for example, irregular food consumption or exercise. In addition, a physician dealing with a particular diabetic individual may require detailed information on the lifestyle of the individual to provide effective treatment or modification of treatment for controlling diabetes. Currently, one of the ways of monitoring the lifestyle of an individual with diabetes has been for the individual to keep a paper logbook of their lifestyle. Another way is for an individual to simply rely on remembering facts about their lifestyle and then relay these details to their physician on each visit.

The aforementioned methods of recording lifestyle information are inherently difficult, time consuming, and possibly inaccurate. Paper logbooks are not necessarily always carried by an individual and may not be accurately completed when required. Such paper logbooks are small and it is therefore difficult to enter detailed information requiring detailed descriptors of lifestyle events. Furthermore, an individual may often forget key facts about their lifestyle when questioned by a physician who has to manually review and interpret information from a hand-written notebook. There is no analysis provided by the paper logbook to distill or separate the component information. Also, there are no graphical reductions or summary of the information. Entry of data into a secondary data storage system, such as a database or other electronic system, requires a laborious transcription of information, including lifestyle data, into this secondary data storage. Difficulty of data recordation encourages retrospective entry of pertinent information that results in inaccurate and incomplete records.

There currently exist a number of portable electronic devices that can measure glucose levels in an individual and store the levels for recalling or uploading to another computer for analysis. One such device is the Accu-Check™ Complete™ System from Roche Diagnostics, which provides limited functionality for storing lifestyle data. However, the Accu-Check™ Complete™ System only permits a limited selection of lifestyle variables to be stored in a meter. There is a no intelligent feedback from values previously entered into the meter and the user interface is unintuitive for an infrequent user of the meter.

SUMMARY OF THE DISCLOSURE

In an embodiment, a method of notifying a user of high or low trends in blood glucose values obtained with a diabetes management unit is provided. The unit includes a microprocessor coupled to a display, memory and user interface buttons. The method can be achieved by: performing with the microprocessor, a plurality of blood glucose measurements of the user; storing in the memory, the plurality of blood glucose measurements; determining whether a most recent blood glucose measurement at a given time during a day is below a first threshold or above a second threshold; evaluating with the microprocessor, whether at least one blood glucose measurement of the plurality of blood glucose measurements performed within a time frame of X hours about the given time of the most recent blood glucose measurement over a period of N days, is lower than the first threshold or higher than the second threshold; and upon achievement of the evaluating step, annunciating that in the same time frame of at least two days over the N number of days, the plurality of blood glucose measurements indicates a blood glucose trend lower than the low threshold or a blood glucose trend higher than a second threshold.

In yet a further embodiment, a diabetes management system is provided that includes a glucose test strip and a diabetes management unit. The diabetes management unit includes a housing, test strip port, plurality of user interface buttons and a microprocessor. The housing includes a test strip port configured to receive the glucose test strip. The microprocessor is coupled to the test strip port to provide data regarding an amount of glucose measured in a user's physiological fluid deposited on the test strip, the microprocessor further coupled to a memory, and user interface buttons. The microprocessor is programmed to: (a) perform a plurality of blood glucose measurements from the user; (b) store the plurality of blood glucose measurements; (c) determine whether a most recent blood glucose measurement at a given time during a day is below a first threshold or above a second threshold; (d) evaluate whether at least one blood glucose measurement of the plurality of blood glucose measurements performed within a time frame of X hours about the given time as the most recent blood glucose measurement over a period of N days, is lower than the first low threshold or higher than the second threshold; and (e) annunciate, upon achievement of the evaluation, that in the same time frame of at least two days over the N number of days, the plurality of blood glucose measurements indicates a trend lower than the low threshold or a trend higher than a second threshold.

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE FIGURES

The accompanying drawings, which are incorporated herein and constitute part of this specification, illustrate presently preferred embodiments of the invention, and, together with the general description given above and the detailed description given below, serve to explain features of the invention (wherein like numerals represent like elements).

FIGS. 2A, 2B, 2C, and 2D illustrate an overview of a process flow for a user interface of the diabetes data management unit.

FIG. 6B illustrates various screens and user interface flows with alternate high trend messages that are presented to the user.

DETAILED DESCRIPTION OF THE EXEMPLARY FIGURES

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment.

Figure 1A:
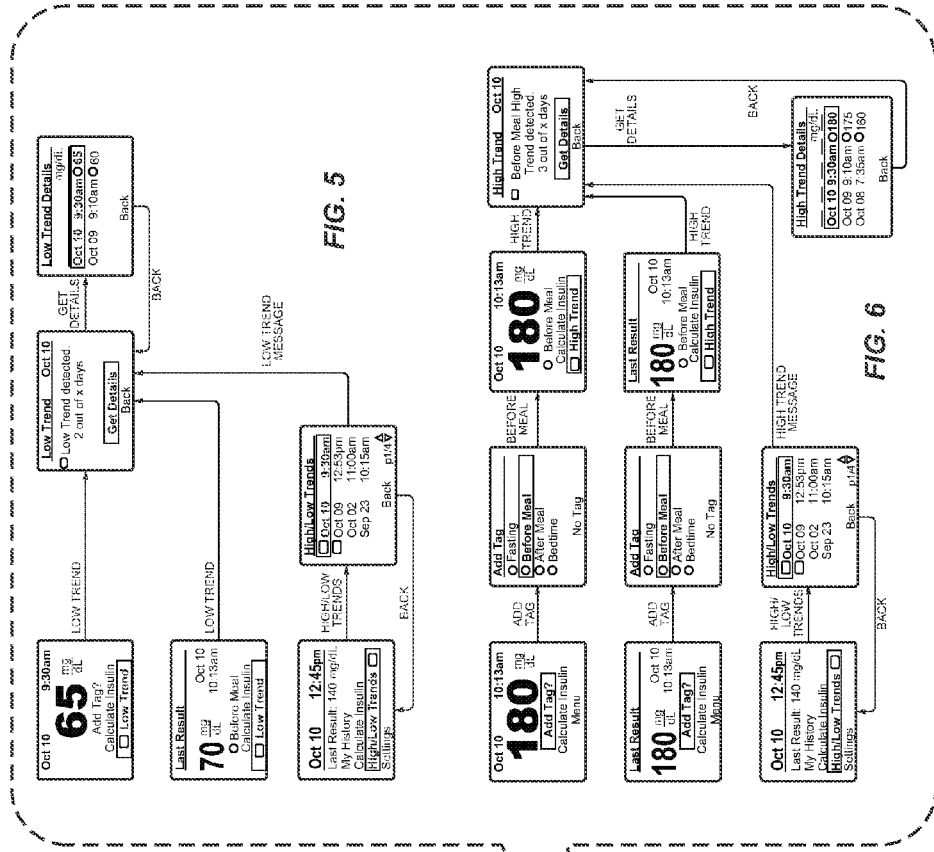
FIG. 1A illustrates a diabetes management system that includes an analyte measurement and data management unit and a biosensor.
Figure 1A:
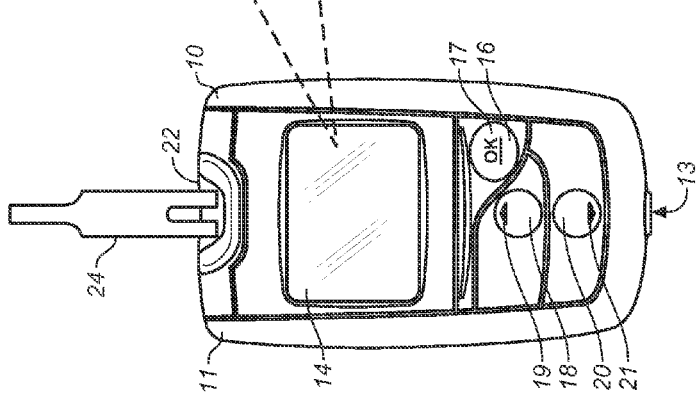

FIG. 1A illustrates a diabetes management system that includes a diabetes data management unit 10 ("DMU") and a biosensor in the form of a glucose test strip 24. Glucose meter or DMU 10 can include a housing 11, user interface buttons (16, 18, and 20), a display 14, a strip port connector 22, and a data port 13, as illustrated in FIG. 1A. User interface buttons (16, 18, and 20) can be configured to allow the entry of data, navigation of menus, and execution of commands. Data can include values representative of analyte concentration, and/or information, which are related to the everyday lifestyle of an individual. Information, which is related to the everyday lifestyle, can include food intake, medication use, occurrence of health check-ups, and general health condition and exercise levels of an individual. Specifically, user interface buttons (16, 18, and 20) include a first user interface button 16, a second user interface button 18, and a third user interface button 20. User interface buttons (16, 18, and 20) include a first marking 17, a second marking 19, and a third marking 21, respectively, which allow a user to navigate through the user interface. Although the buttons are shown as mechanical switches, a touch screen with virtual buttons may also be utilized. As represented in FIG. 1A, the DMU is provided with various user-interfaces including the user interface for high and low blood glucose trends of FIGS. 5 and 6.

Figure 1B:
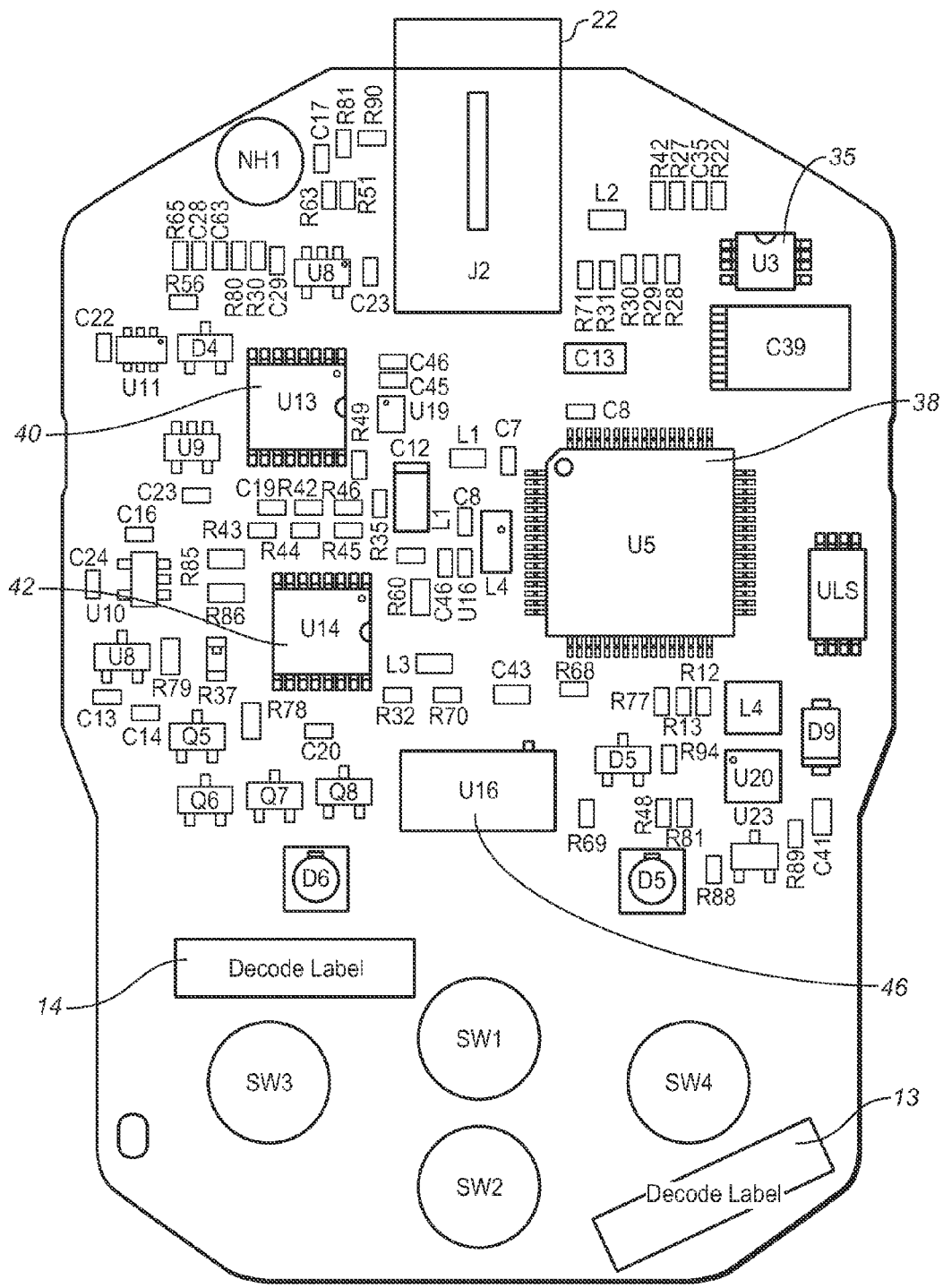
FIG. 1B illustrates, in simplified schematic, an exemplary circuit board of a diabetes data management unit.

The electronic components of meter 10 can be disposed on a circuit board 34 that is within housing 11. FIG. 1B illustrates (in simplified schematic form) the electronic components disposed on a top surface of circuit board 34. On the top surface, the electronic components include a strip port connector 22, an operational amplifier circuit 35, a microcontroller 38, a display connector 14a, a non-volatile memory 40, a clock 42, and a first wireless module 46. On the bottom surface, the electronic components may include a battery connector (not shown) and a data port 13. Microcontroller 38 can be electrically connected to strip port connector 22, operational amplifier circuit 35, first wireless module 46, display 14, non-volatile memory 40, clock 42, battery, data port 13, and user interface buttons (16, 18, and 20).

Operational amplifier circuit 35 can include two or more operational amplifiers configured to provide a portion of the potentiostat function and the current measurement function. The potentiostat function can refer to the application of a test voltage between at least two electrodes of a test strip. The current function can refer to the measurement of a test current resulting from the applied test voltage. The current measurement may be performed with a current-to-voltage converter. Microcontroller 38 can be in the form of a mixed signal microprocessor (MSP) such as, for example, the Texas Instrument MSP 430. The MSP 430 can be configured to also perform a portion of the potentiostat function and the current measurement function. In addition, the MSP 430 can also include volatile and non-volatile memory. In another embodiment, many of the electronic components can be integrated with the microcontroller in the form of an application specific integrated circuit (ASIC).

Strip port connector 22 can be configured to form an electrical connection to the test strip. Display connector 14a can be configured to attach to display 14. Display 14 can be in the form of a liquid crystal display for reporting measured glucose levels, and for facilitating entry of lifestyle related information. Display 14 can optionally include a backlight. Data port 13 can accept a suitable connector attached to a connecting lead, thereby allowing glucose meter 10 to be linked to an external device such as a personal computer. Data port 13 can be any port that allows for transmission of data such as, for example, a serial, USB, or a parallel port. Clock 42 can be configured to keep current time related to the geographic region in which the user is located and also for measuring time. The DMU can be configured to be electrically connected to a power supply such as, for example, a battery.

In one exemplary embodiment, test strip 24 can be in the form of an electrochemical glucose test strip. Test strip 24 can include one or more working electrodes and a counter electrode. Test strip 24 can also include a plurality of electrical contact pads, where each electrode can be in electrical communication with at least one electrical contact pad. Strip port connector 22 can be configured to electrically interface to the electrical contact pads and form electrical communication with the electrodes. Test strip 24 can include a reagent layer that is disposed over at least one electrode. The reagent layer can include an enzyme and a mediator. Exemplary enzymes suitable for use in the reagent layer include glucose oxidase, glucose dehydrogenase (with pyrroloquinoline quinone co-factor, "PQQ"), and glucose dehydrogenase (with flavin adenine dinucleotide co-factor, "FAD"). An exemplary mediator suitable for use in the reagent layer includes ferricyanide, which in this case is in the oxidized form. The reagent layer can be configured to physically transform glucose into an enzymatic by-product and in the process generate an amount of reduced mediator (e.g., ferrocyanide) that is proportional to the glucose concentration. The working electrode can then measure a concentration of the reduced mediator in the form of a current. In turn, glucose meter 10 can convert the current magnitude into a glucose concentration. Details of the preferred test strip are provided in U.S. Pat. Nos. 6,179,979; 6,193,873; 6,284,125; 6,413,410; 6,475,372; 6,716,577; 6,749,887; 6,863,801; 6,890,421; 7,045,046; 7,291,256; 7,498,132, all of which are incorporated by reference in their entireties herein.

Figure 2B:
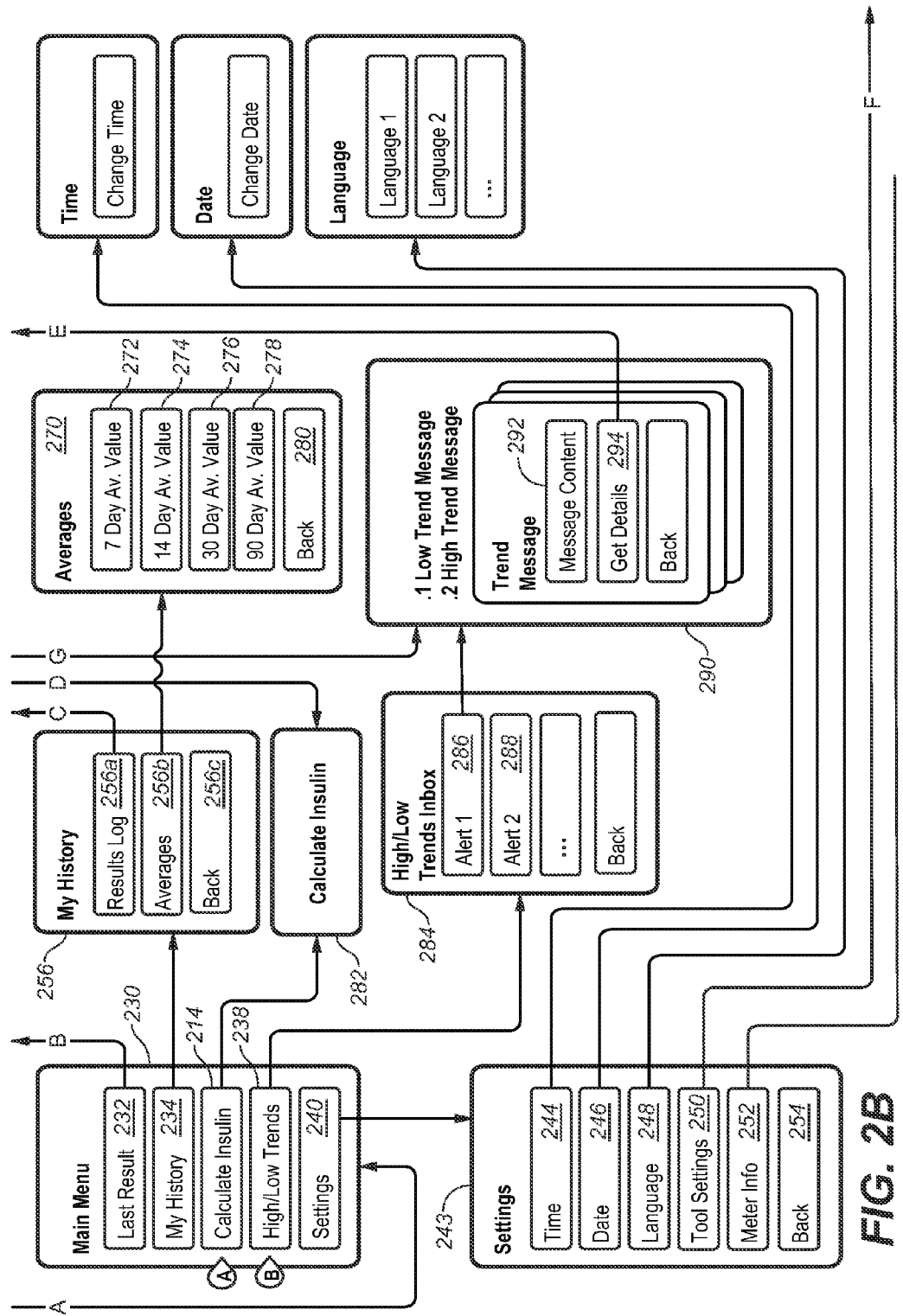
Figure 2C:
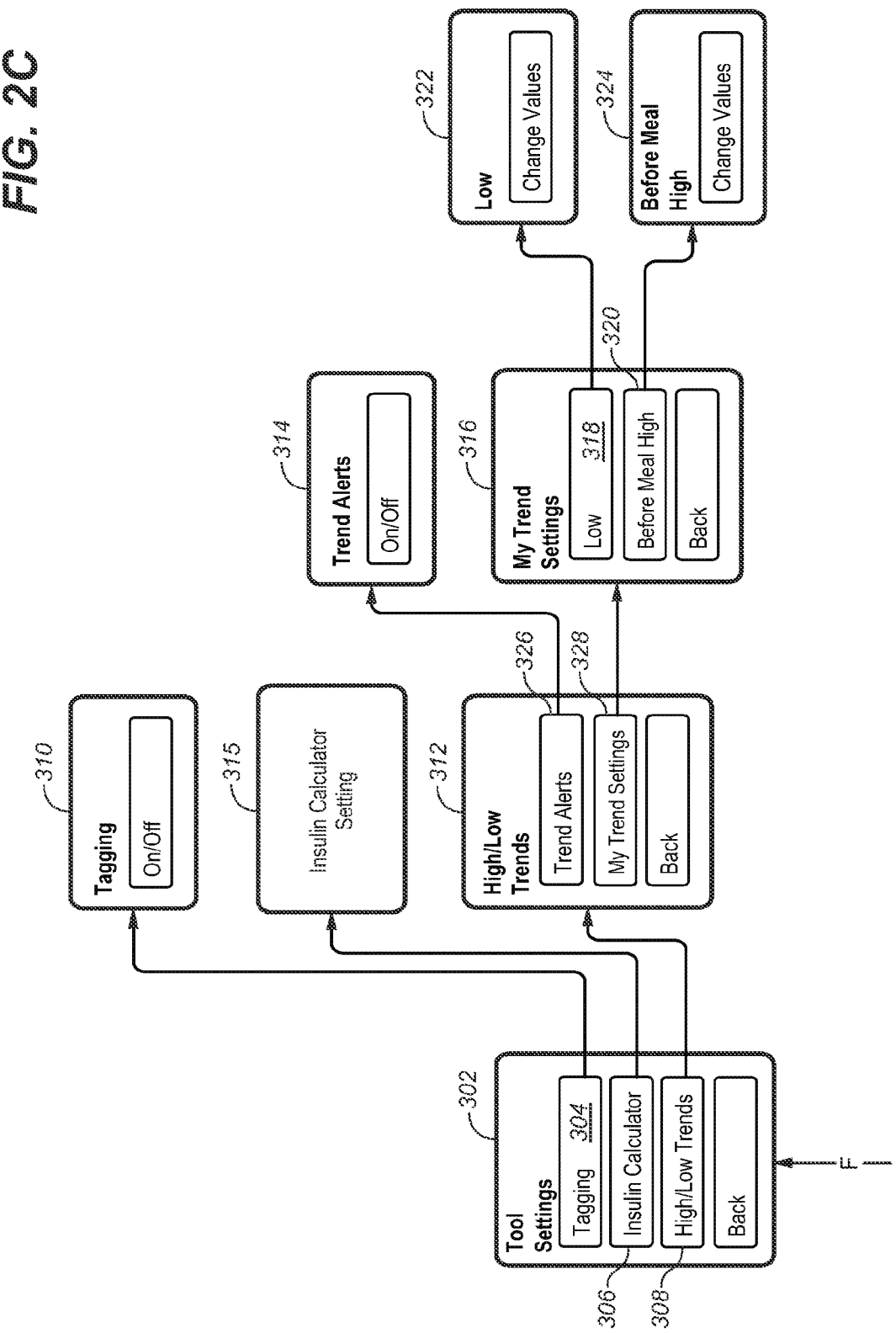

Referring to FIGS. 2A, 2B, 2C, and 2D, an exemplary process flow of portions of the user interface for the DMU is provided. Specifically, in FIG. 2A, the process flow begins at 200 when a suitable test strip 24 is inserted into the DMU 10. A blood glucose ("BG") result at 202 is annunciated to the user. As used here, the term "annunciated" and variations on the root term indicate that an announcement may be provided via text, audio, visual or a combination of all modes of communication to a user. The BG reading 204 is stored for use in screen 206 which allows the user to scroll through a menu starting with a recall of a previous BG result 208, adding or editing a tag or flag 210, obtaining a trend alert 212, calculate insulin bolus 214, and returning to a main menu 216. Some of the functionalities 212-214 on the menu 206 may not be available depending on whether one or more of such functionalities have been enabled in the main menu. Where an edit to or addition of a flag 210 is desired for a BG result, the following selections are available: a fasting flag 210a (e.g., a BG result obtained during a fasting period of at least 6-8 hours); a before meal flag 210b (e.g., a BG result obtained prior to a meal); an after meal flag 210c; a bedtime flag 210d or no tag 210e.

Where the user desires to access a main menu of the DMU, an actuation at 220 of one of the buttons of the DMU over a long duration (e.g., greater than 2 seconds) can be utilized to allow access to the main menu 230 in FIG. 2B. In main menu 230, the following functionalities may be available to the user or a health-care-provider ("HCP"): last blood glucose result 232, historical BG results 234, calculate insulin dosing 214, provide indicator of high or low trends 238, and device settings 240. Should a last blood glucose result 232 be selected, the process flows to results screen 242. In this screen 242, the following functionalities are available to the user: a last BG result 244 or historical results 246. In screen 246, the last BG reading is provided along with the ability to select an add or edit of tag 210, trend alert 212, calculate insulin 214, or returning to previous menu screen 230.

Referring to FIG. 2B, the remainder of the available functionalities of screen 230 will be described. Where a history of the BG results are desired, screen 256 is provided to allow for selection of a log of results 256a collected or performed by the DMU; averages of the BG results 256b based on user's defined parameters. As is the norm for user interfaces, a previous screen selection 256c is also provided. Where the results log 256a is selected, screen 260 (FIG. 2A) is provided that annunciates a range of results 262, 264 and subsequent series of results. Referring back to FIG. 2B, where the averages 256b of the results stored in the device are desired, screen 270 is provided that allows for a display of various ranges of average BG results. For example, a 7-day average; 14-day average; 30-day average; 90-day average are provided; any range as desired by the user or HCP. Alternatively, a median for each of the pre-defined date ranges may also be provided in addition to the average for each of the date ranges.

Where the user desires to calculate insulin bolus, the device can activate a calculation protocol 282 to provide a calculated insulin bolus. Three types of insulin boluses are described herein: (a) carbohydrate coverage, (b) glucose correction, or (c) a combination thereof. The insulin bolus amount for carbohydrate coverage may be an amount of insulin needed to account for carbohydrates about to be consumed at a meal. The insulin bolus amount for a glucose measurement correction may be an amount of insulin needed to account for a user's measured glucose value that is greater than a targeted euglycemic glucose value. The combination (e.g., carbohydrate value and measured glucose value) correction may be an amount of insulin needed to account for carbohydrates about to be consumed and the user's measured glucose value.

The glucose correction dose is an amount of insulin needed to account for a user's recently measured glucose value that is greater than the euglycemic zone. The carbohydrate coverage dose is an amount of insulin calculated based on the amount of carbohydrates to be consumed. The combination (e.g., carbohydrate value and measured glucose value) correction may be an amount of insulin needed to account for carbohydrates about to be consumed and the user's measured glucose value. Details of the insulin dosing calculation are provided in U.S. Provisional Patent Applications Ser. No. 61/246,630 filed 29 Sep. 2009, Ser. No. 61/297,573 filed 22 Jan. 2010, and Ser. No. 61/308,196, filed Feb. 25, 2010, all of the applications are hereby incorporated into this application.

Referring back to FIG. 2B, screen 230 allows for the user to select a high/low trends screen 238. Screen 238 allows the user to view the various alerts 286, 288 and subsequent series, provided to the user. Selection of a specific alert, for example, alert 286 allows the user to view screen 290 which includes message content 292, and details of the message 294. Selection of details 294 allows the user to proceed to screen 296 which includes a history of BG results 298, 300, and subsequent series of results.

Where a device setting 240 is desired, screen 243 is provided to allow for the selection of the following user's adjustable settings: time 244, date 246, language 248, and tool settings 250. A device information selection 252 and a previous screen selection 254 are also provided in screen 243. The tool setting selection 250 allows the user or a HCP to set up the DMU 10 for the user. In particular, once tool setting functionality 250 is selected, screen 302 is provided to allow for selection of various settings including set up for tagging or flagging field 304; set up for insulin calculation field 306; and set up for high/low trends field 308. To turn on the tagging or flagging function, screen 310 allows for the user to turn this feature on or off by scrolling a pointer over to field 304 in screen 302. To modify the insulin calculation, the user must scroll a pointer to field 306 for the process flow to switch over to screen 315. To modify the high/low trends alert, the user must scroll a pointer to field 308 for the process flow to switch over to a screen 312. Once high/low trends 308 is selected, screen 312 is provided to allow for selection of various settings including Trend Alerts 326 and My Trend Settings 328. To activate Trend Alerts 326, screen 314 allows for the user to turn this feature on or off. To adjust My Trend Settings 328, screen 316 allows for the user modify the thresholds. Modification to the thresholds can be made via screen 316 by selection of field 318 to modify a prestored low threshold at screen 322, or modify a prestored high setting by selection of field 320. As an exemplary embodiment, the modification to the high and low thresholds for trends functionality, reference is made to FIG. 2C.

Figure 2D:
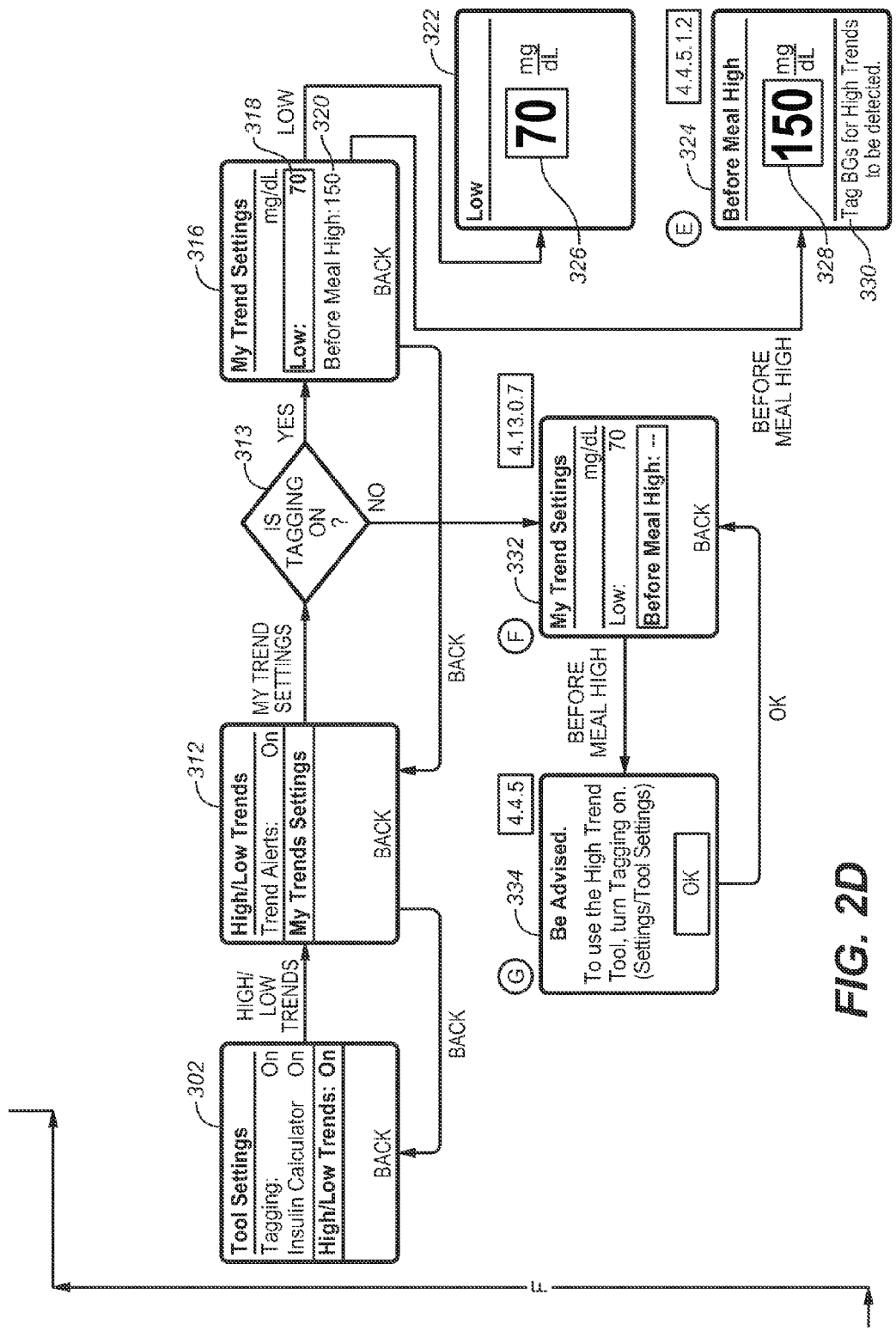

In FIG. 2D, a user may select the tool settings screen 302 and highlight the "High/Low Trends: ON" functionality in order to modify the presets first and second thresholds (e.g., approximately 70 milligrams of glucose per deciliter of blood for the first threshold and approximately 150 milligrams of glucose per deciliter of blood for the second threshold). Upon selection of the highlighted field, screen 312 is displayed. Upon selection of the field "My Trend Settings," a logical check is made at 313 to determine whether the tagging or flagging of a blood glucose measurement is enabled. If true, screen 316 displays the first threshold and the second threshold. Selection of the first threshold 318 will display screen 322 to allow the user or HCP to change the prestored first threshold numerical value 326 in screen 322. Selection of the second threshold 320 in screen 316 will allow the user or HCP to change the prestored second threshold numerical value 328 in screen 324. A message 330 is also provided to remind the user to tag or flag a BG measurement in order for high trends to be detected by the unit.

On the other hand, where the logical operation at 313 returns a no, the unit is programmed to prevent enablement of the second threshold in screen 332 unless the tagging functionality is turned on. Should the user persist in selecting the blank second threshold, a message is displayed in screen 334 to the effect that the tagging functionality must be enabled in order for high trends to be detected. This is intended to help users understand the relationship between the Before Meal limit and tagging. In other words, if tagging of before meal measurements are not made, then there is little value in providing high trend messages. Additionally, even if tagging is enabled, the user is reminded by message 330 that tagging should be used consistently in order for the before meal high trend to be of value to the user.

Figure 3:
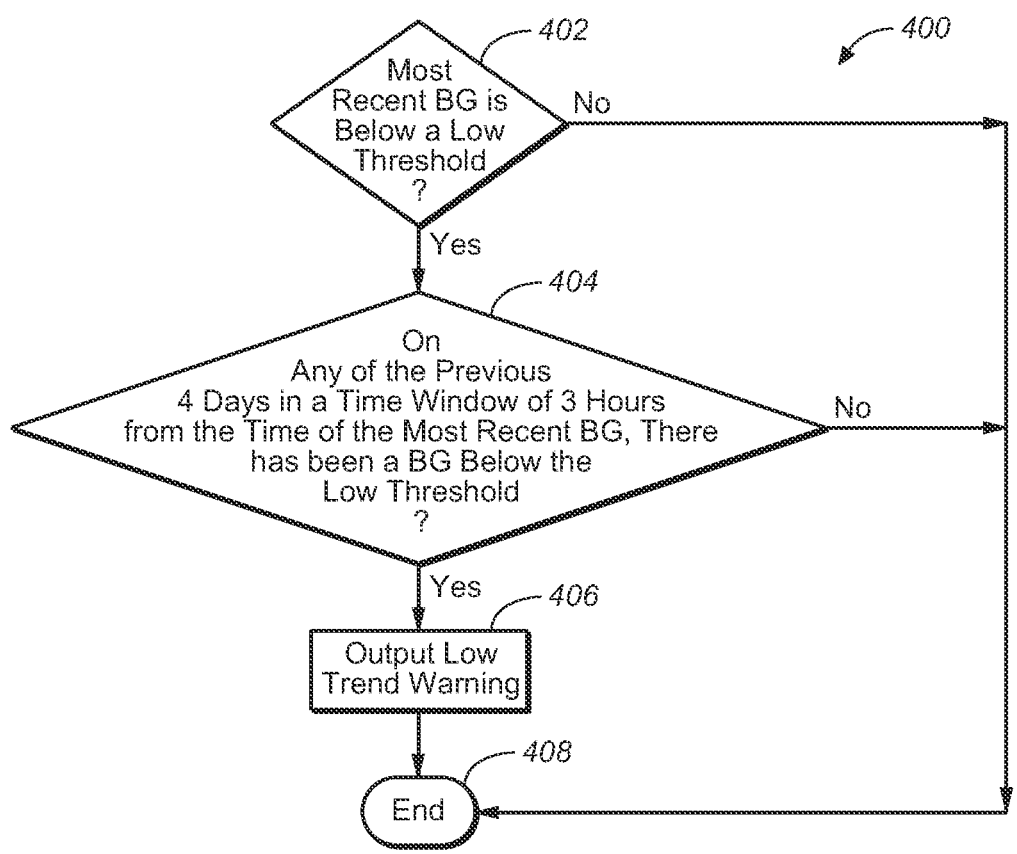
FIG. 3 illustrates a routine 400 to provide a low blood glucose measurements trend.
Figure 5A:
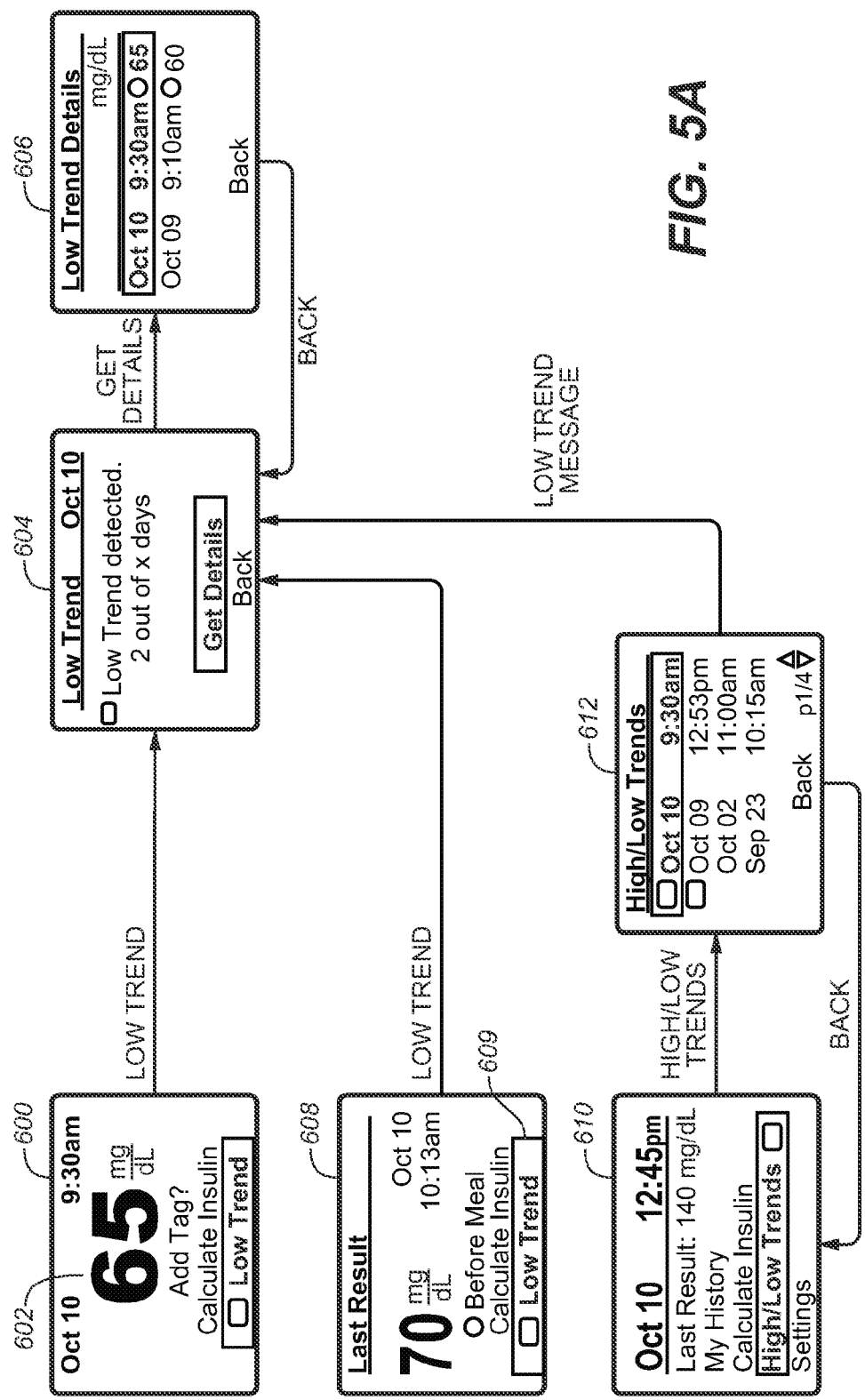
FIG. 5A illustrates various screens and user interface flows for a low blood glucose trend alert.

In operation, a user would conduct a blood glucose measurement (200 in FIG. 2A) and the BG result would be displayed (202). For example, the most recent BG result is shown here in FIG. 5A as 65 mg/dL taken at 930 AM on screen 600. Alternatively, with reference to FIG. 5A, a user could recall a most recent BG result at screen 608. At this point, the microprocessor would utilize the logic of FIG. 3. In FIG. 3, the instant or most recent BG is compared at 402 to determine whether such BG result is below the first threshold. If true at 402 then the microprocessor determines at 404 whether at least one or more of the plurality of blood glucose measurements made within a window of X hours (e.g., approximately 3 hours from about 8 AM to about 11 AM) bracketing the same time period (9:30 AM) as the most recent BG measurement 602 were made in the most recent N number of days is lower than the first threshold. In the example of FIG. 5A, the BG result is 65 mg/dL which is below the preset first threshold of about 70 mg/dL. The BG was taken at about 9:30 AM. On the basis of the logic described herein, the microprocessor will look to its stored blood glucose measurements that were taken at a time frame of X hours bracketing the time (i.e., about 930 AM) at which the most recent blood measurement was made in the previous N number of days to determine whether at least one blood glucose measurement in such bracketed time frame about the given time (i.e., 930 AM) is lower than the first threshold. If at least one prior measurement fits this condition, the microprocessor annunciates a message 406 to warn of a low trend. In particular, as shown in FIG. 5A, at screen 604, a text message indicates that a low trend has been detected for at least 2 days out of N number of days for the same time frame bracketing the given time at which most recent blood glucose measurement of 65 mg/dL was made. Where a user desires to view a last blood glucose result, screen 608 may be displayed and a selection for a low trend message 609 can be selected. In such selection, screen 604 provides for a general indication that a low trend has been detected, as illustrated in FIG. 5A. The user may select "Get Details" in screen 604 in order to see details around the detection of the low trend such as, for example, a table listing the date, time, and value of the BG results as shown on screen 606. Where a user is viewing menu screen 610, the user may select from screen 610 a general indication at screen 612 that one of either high or low trend has been detected on a listing of date and time. To view the details of this general alert, the user would select a specific date such as October 10 at 930 AM, which would provide a generalized indication that the general alert relates to a low trend. For details, the user may select screen 606 in order to see details around the detection of the low trend such as, for example, a table listing the date, time, and value of the BG results as shown on screen 606.

Figure 5B:
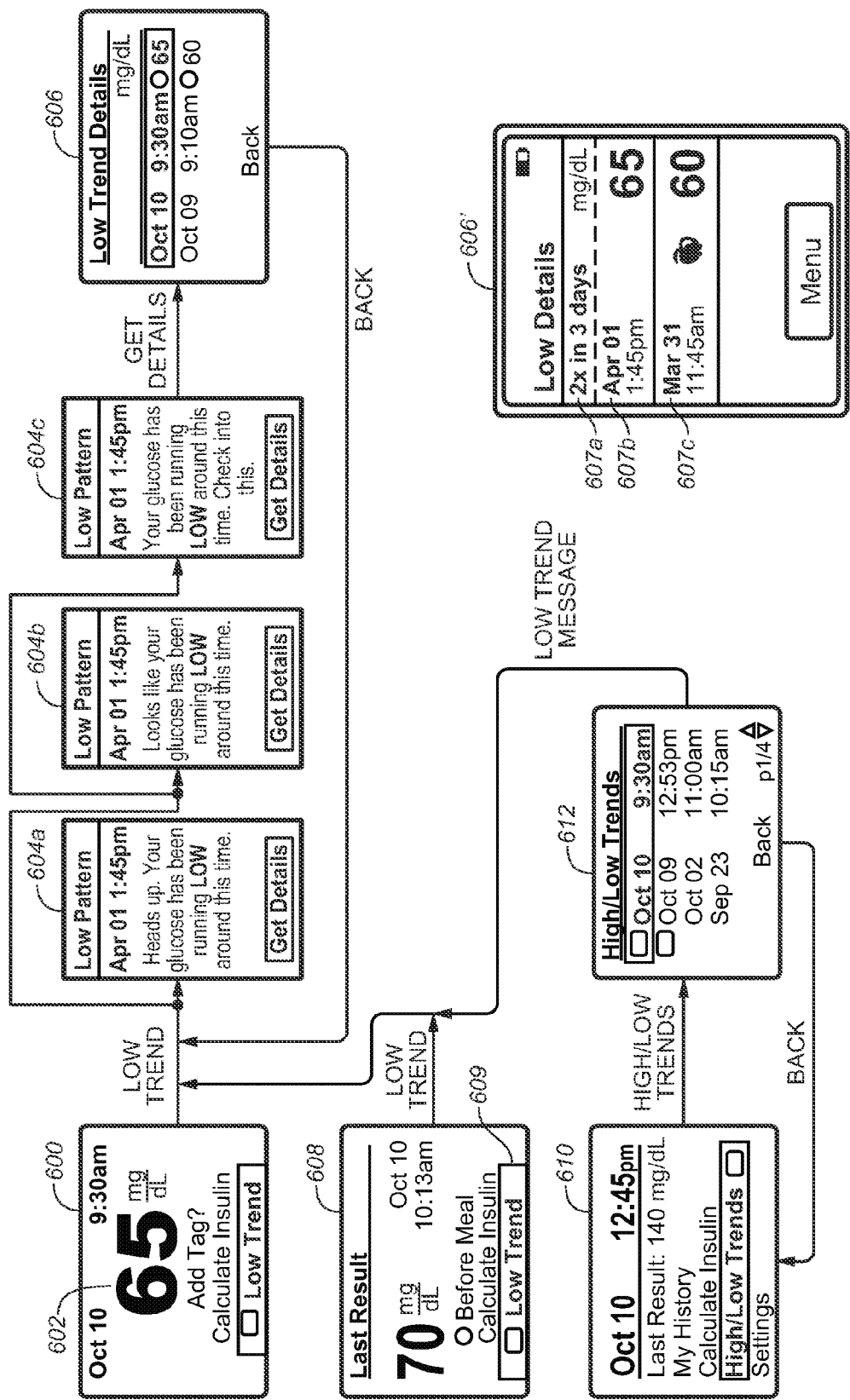
FIG. 5B illustrates various screens and user interface flows with alternate low trend messages that are presented to the user.

In an alternative embodiment, at least three different screens (604a, 604b, 604c) in FIG. 5B can be utilized in place of message 604 of FIG. 5A. In this alternative, a first message 604a (e.g., "Heads up. Your glucose has been running LOW around this time") can be annunciated to the user. On a different occasion where a low trend message is warranted, message 604b (e.g., "Looks like your glucose has been running LOW around this time") with semantically the same meaning of message 604a can be annunciated to the user instead of message 604a itself. On yet another occasion where a low trend message according the logic described herein is warranted, message 604c (e.g., "Your glucose has been running LOW around this time. Check into this") can be utilized in place of either of messages 604a and 604b. As previously described, the user may select "Get Details" in any one of screen 604a, 604b, or 604c in order to see details around the detection of the low trend such as, for example, a table listing the date, time, and value of the BG results as shown on screen 606. An alternative screen 606' can be provided instead of screen 606. In this screen 606', the details are provided as a number of time the user has been low in partition 607a of screen 606'; the particular date and time of the low readings in respective partitions 607b and 607c. Additional information can also be provided in each of the partition such as, for example, the value on which a low determination was based and whether the reading was taken with a tag of before meal (indicated by a suitable icon such as, for example, an uneaten fruit, such as, for example, an apple). It is noted that differently formatted messages 604a, 604b, 604c, and the like may be displayed in a fixed order as shown or in a random order for low trend pattern messages so that the user is not perceiving the identical message over and over again, which may lulls the user into ignoring the point that there is a high trend for the user's blood glucose values.

Figure 4:
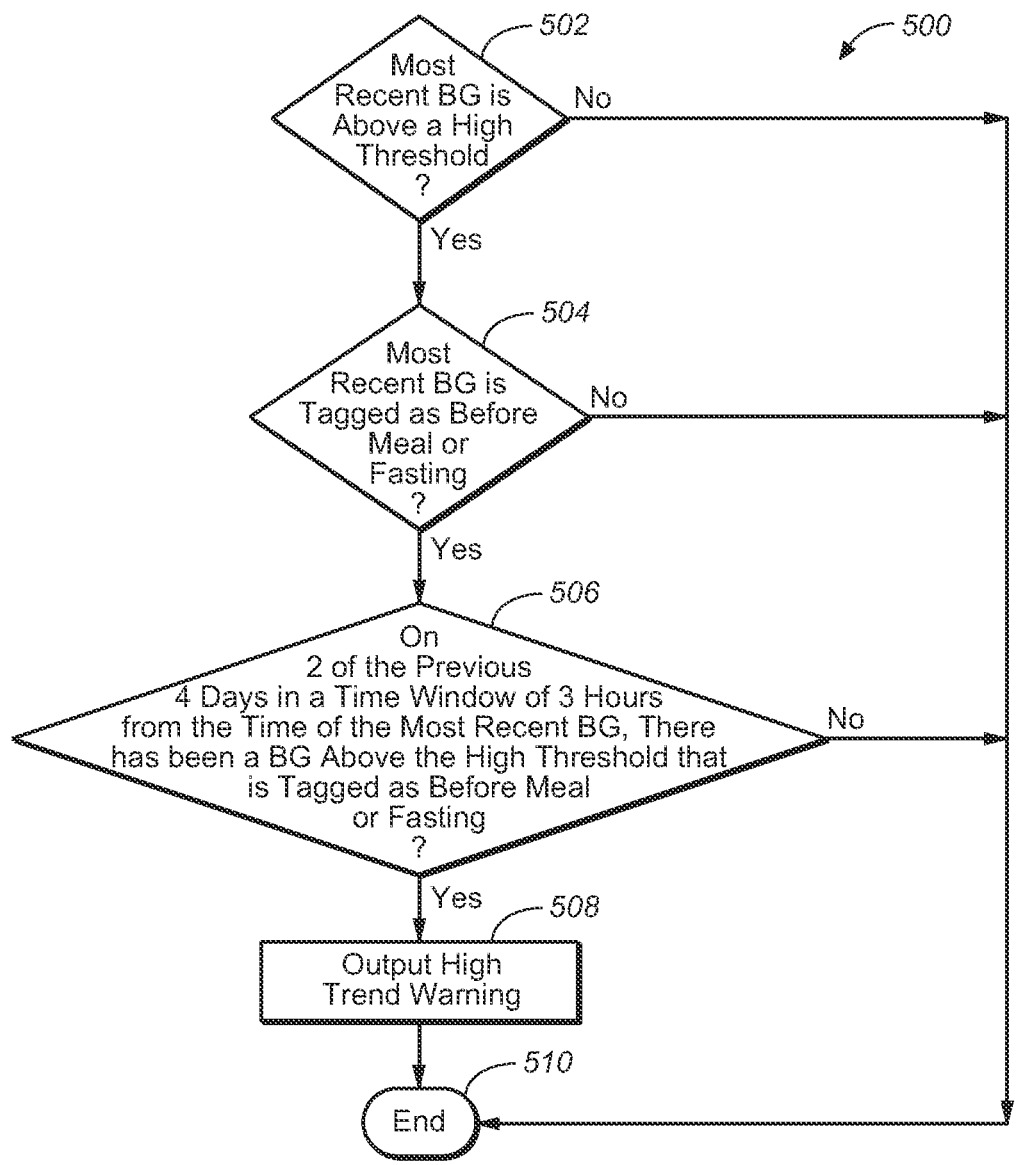
FIG. 4 illustrates a routine 500 to provide a high blood glucose measurements trend.
Figure 6A:
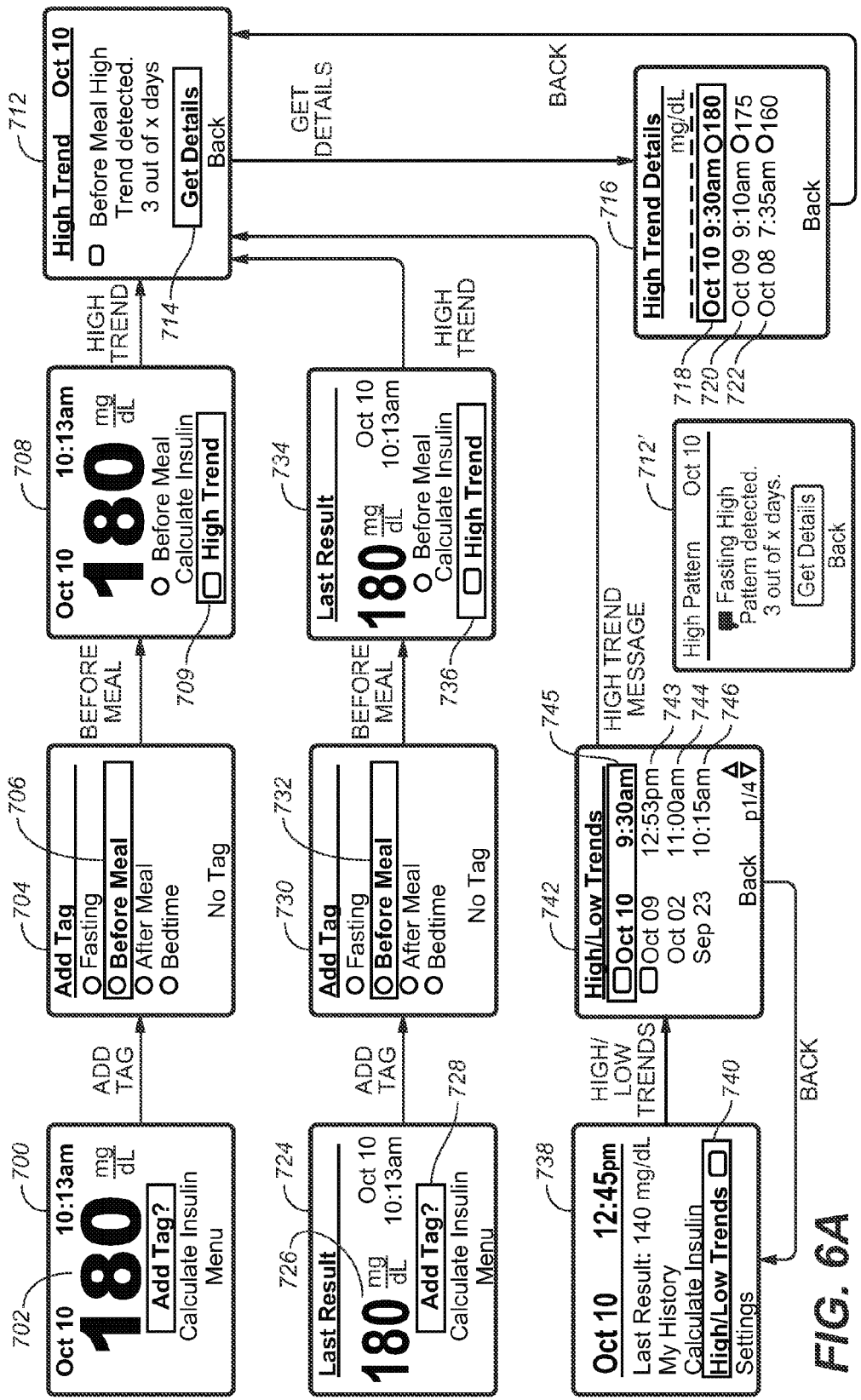
FIG. 6A illustrates various screens and user interface flows for a high blood glucose trend alert.
Figure 6C:
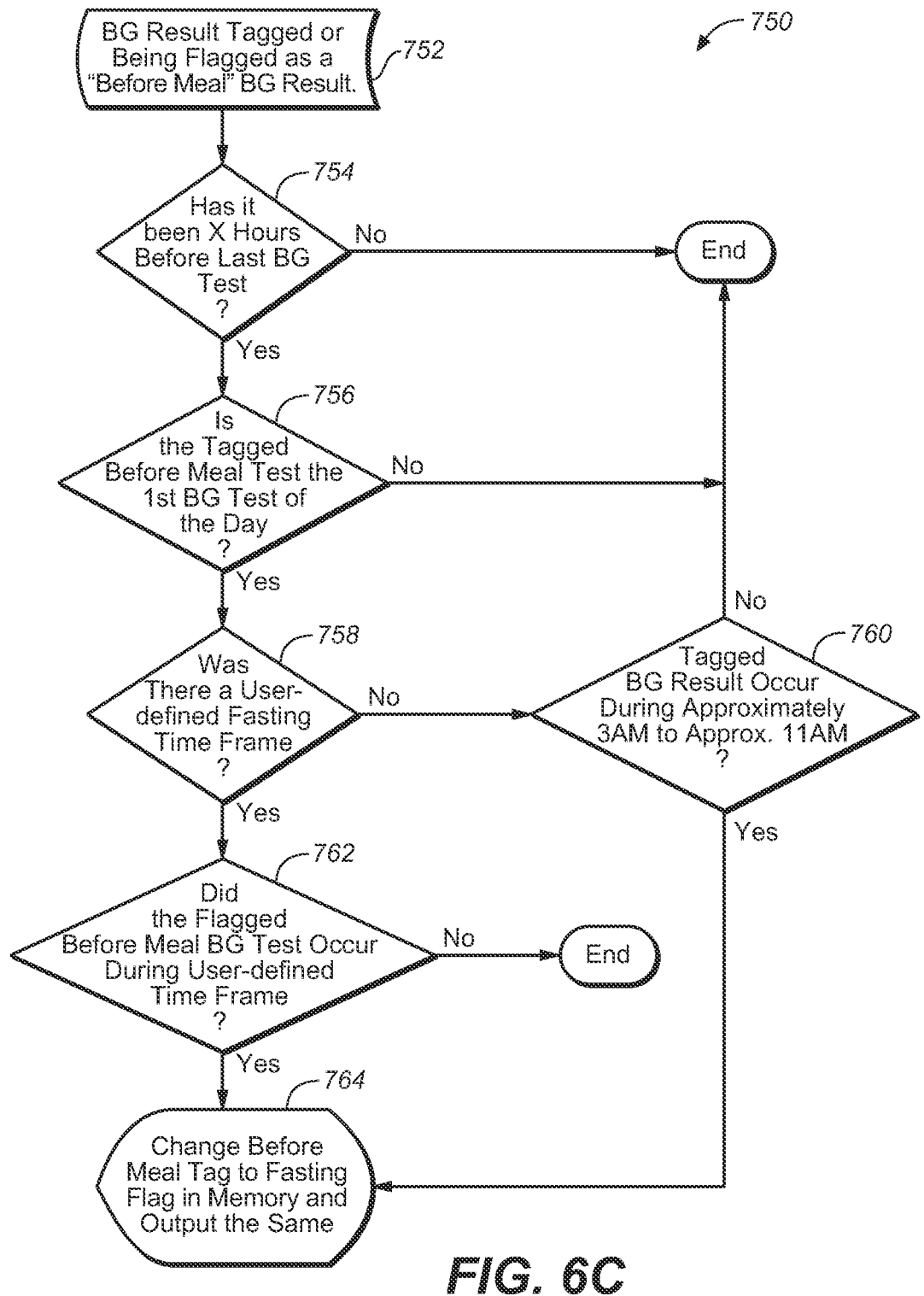
FIG. 6C illustrates a logic flow to determine whether a Before Meal BG result should be flagged or tagged as a Fasting BG result.

On the other hand, with reference to FIGS. 4, 6A and 6B, if the most recent BG measurement is above a high or second threshold and such recent BG was or being tagged as one of "fasting" or "before meal" then the microprocessor polls for previously stored blood glucose measurements made in the previous N number of days within a windows of X hours bracketing the same time period (e.g., 10:13 AM) in which the most recent BG measurement of 180 mg/dL was made. In the example of FIG. 6A, the most recent BG (at 702) is shown on screen 700 as 180 mg/dL which is higher than the preset second threshold of about 170 mg/dL. Here, the most recent BG is being tagged at screen 704 as being a "Before Meal" measurement at selection field 706. Since both conditions (i.e., greater than the second threshold and tagged as one of before meal or fasting) have been met, the microprocessor polls the previously stored blood glucose measurements made in the previous N number of days over a time window of X hours bracketing the time (10:13 AM) at which the most recent and tagged BG measurement was made. If there is at least one prior glucose measurement greater than the second threshold in the window of time (e.g., about 3 hours) bracketing the same time at which the most recent BG was taken, then screen 708 provides for a general alert that a high trend has been detected. In another embodiment, two or more prior glucose measurements greater than the second threshold can be required in the window of time (e.g., about 3 hours) bracketing the same time at which the most recent BG was taken to trigger a high trend alert. For details of this trend, the user is invited to select field 709 which provides screen 712. Screen 712 indicates that in 3 of N number of days there is a trend of high BG values at around the same time in each of those 3 days. The user can obtain even more details of the trend by selecting field 714 which provides for screen 716. Screen 716 shows, for example, a table of the three BG measurements 718, 720, 722, and the corresponding dates and times. Alternatively, a screen 716' can be utilized instead of screen 716 to provide more information to the user. In this screen 716', the details are provided as a number of time the user has been low in partition 717 of screen 716'; the particular date and time of the low readings in respective partitions 718', 720', and 722'. Additional information can also be provided in each of the partition such as, for example, the exact value on which a high glucose determination was based and whether the reading was taken with a tag of before meal (indicated by a suitable icon such as, for example, an uneaten fruit, such as, for example, an apple).

In an alternate embodiment of FIG. 6B, instead of a single message 712 as in FIG. 6A, there are at least three differently formatted messages that may be presented to the user in sequence or in a random sequence. In particular, at least three differently formatted messages 712a, 712b, and 712c are utilized to communicate semantically a similar message. For example, message 712a (e.g., "Heads up, your Before meal (or Fasting) glucose value has been running high around this time") may be provided when the user has selected field 709. On a different occasion when the user has again selected field 709, message 712b (e.g., "Your Before Meal (or Fasting) glucose has been running HIGH around this time. Check into this") may be provided instead of 712a. Similarly, on yet a different occasion when the user has selected field 709, message 712c (e.g., "Heads up. Around this time your glucose has been running HIGH before meals (or during fasting)") may be provided in lieu of 712b.

Messages 712a, 712b, 712c and the like may cycle sequentially or randomly so that the user does not perceive the identically formatted message over and over again, which may lulls the user into ignoring the main point in that there is a high trend for the user's blood glucose values.

In a scenario where the user is viewing the last blood glucose result, screen 724 is provided which allows the user the option of tagging this last blood glucose result at field 728. Screen 730 provides a menu of tagging fields. Once the user selects a "Before Meal" tag 732, screen 734 provides a general alert that a high trend has been detected at 736. Selection of field 736 causes screen 712 to display a more detailed indication that in 3 of N number of days there is a trend of high BG values at around the same time bracket in each of those 3 days.

Even though the user may select either a "Before Meal" tag or a "Fasting" tag, the microprocessor may be programmed to automatically infer that certain blood glucose measurements are measurements taken during a fasting period. In particular, with reference to the logic flow 750 FIG. 6C, if the subject measurement was tagged at 752 as a Before Meal measurement N hours since the last blood glucose test or measurement at 754, AND the Before Meal tagged measurement was the first test of the day at 756, based on the clock of the DMU within a user's preset time frame of certain hours in the day, at 758, then the subject measurement is modified to show a Fasting tag at 764. The value "N" can be any value from ½ hour to 8 hours and the time frame can be any range defined by specific clock times (e.g., 1 AM to 8 AM in 810) or preset, such as, for example 3:00 AM to 11:00 AM. Consequently, where the fasting measurements are showing a high trend according to the illustrated logic 750 of FIG. 6C, a different message than message 712 in FIG. 6A may be presented. For example, a message 712' that "Fasting High" pattern has been detected in a number of times in a given number of days can be substituted for message 712 in FIG. 6A.

In another scenario where the user is viewing menu screen 738, a general indication 740 can be provided to alert that a high (or fasting high) trend has been detected. Upon selection of field 740, screen 742 shows, for example, a table of the dates and times 743, 744, 745, and 746 that constitute the high trend.

In the preferred embodiments, the window of X hours includes about 6 hours and the N number of days may range from about 2 to about 21 days. In another preferred embodiment, the window of X hours include about 3 hours and the N number of days may range from about 2 to about 30 days, and most preferably from about 2 to about 5 days.

By virtue of the system and processes described herein, a method of notifying a user of high or low trends in blood glucose values obtained with a diabetes management unit is provided. The method may include the steps of: performing with the microprocessor, a plurality of blood glucose measurements; storing in the memory, the plurality of blood glucose measurements; determining whether a most recent blood glucose measurement is below a first threshold or above a second threshold; evaluating with the microprocessor, whether at least one blood glucose measurement of the plurality of blood glucose measurements performed within a time frame as the most recent blood glucose measurement over a period of N days, is lower than the first low threshold or higher than the second threshold; and upon achievement of the evaluating step, annunciating that in the same time frame of at least two days over the N number of days, the plurality of blood glucose measurements indicates a trend lower than the low threshold or a trend higher than a second threshold.

Figure 7:
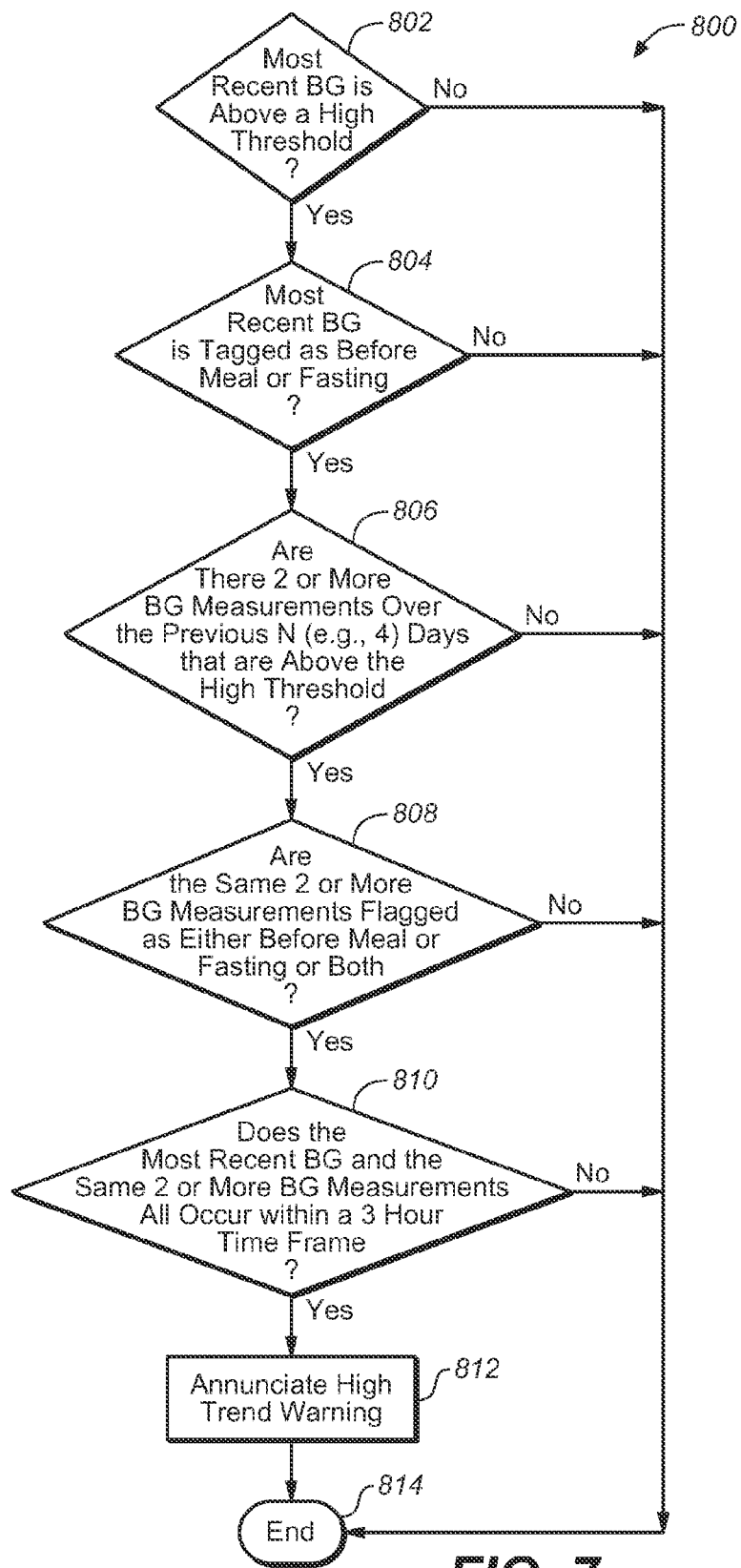
FIG. 7 illustrates an alternative logic flow for high-trend determination.

In a further alternative embodiment, shown here in FIG. 7, a high trend detection logic 800 is provided for the system. In this logic flow, a logical query 802 is made as to whether a most recent BG result is above a high threshold. If true, a logical query 804 as to whether the most recent BG result has been tagged as a Before Meal BG result or a Fasting BG result. If true, the logic flows to query 806 to determine whether 2 or more prior BG measurements over the previous N number of days (e.g., 4 days) that are above the high threshold. If true, the logic flows to query 808 to determine whether the same 2 or more BG results have both been flagged as either a Before Meal BG result or a Fasting BG result. If true, the logic flows to query 810 to determine whether the most recent BG result and the same 2 or more prior BG results all occur within X hours time frame. If true, the logic 800 annunciates a high trend warning at output 812. In queries 802-810, if the logic returns a false then the routine ends at 814. In the preferred embodiments, the variable N can be of any value from about 2 to 90 days and X can be of any value from about 1 hour to about 7 hours.

As an example of the logic 800, it will be assumed that a user conducted a series of measurements from Monday to Friday with a most recent BG result at 9 AM on Friday, as set forth in Table 1 below:

TABLE 1

| Monday-7:50 AM | Exceeds High Threshold |
| | Flagged as Fasting BG result |
| Tuesday-10:49 AM | Exceeds High Threshold |
| | Flagged as Before Meal BG result |
| Wednesday-7:40 AM | Exceeds High Threshold |
| | Flagged as Fasting BG result |
| Thursday-11:30 AM | Exceeds High Threshold |
| | Flagged as Before Meal BG result |
| Friday-9:00 AM | Exceeds High Threshold |
| (Most Recent BG result) | Flagged as Fasting BG result |

Referring to Table 1, the most recent BG has a logical true state for the logical queries 802 and 804 (i.e., exceeds the high threshold and flagged as fasting). At least one BG for each of the last four days has a logical true state for the logical queries 806 and 808. The logical query 810 must evaluate at least three BG's, which are the most recent BG (from queries 802 and 804) and the at least two BG's (from queries 806 and 808).

Based on the results collected in the previous 4 days, a warning message would be annunciated with the most recent BG on Friday at 9:00 AM. The 3 hour time bracket can include, in chronological order for time of day, 7:50 AM (Monday), 9:00 AM (Friday), and 10:49 AM (Tuesday), where the difference between the latest time and the earliest time is less than three hours (10:49 AM minus 7:50 AM=2 hours and 59 minutes). Thus, the Monday, Friday, and Tuesday BG's fall within the three hour time bracket. In addition to Monday, Friday, and Tuesday, the 3 hour time bracket can also include, in chronological order for time of day, 7:40 AM (Wednesday), 7:50 AM (Monday), and 9:00 AM (Friday), where the difference between the latest time and the earliest time is less than three hours (9:00 AM minus 7:40 AM=1 hour and 20 minutes).

Referring back to Table 1, there is no high trend alert for Wednesday. For Wednesday, 2 previous BG's and 1 most recent BG are evaluated in the logical query 810, which are 7:40 AM (Wednesday), 7:50 AM (Monday), and 10:49 AM (Tuesday), where the difference between the latest time and the earliest time is more than three hours (i.e., 10:49 AM minus 7:40 AM=3 hours and 9 minutes). Thus, the Wednesday, Monday, and Tuesday BG's do not fall within the three hour time bracket.

Referring back to Table 1, there is no high trend alert for Thursday. For Thursday, 2 previous BG's and 1 most recent BG are evaluated in the logical query 810. Note that there are three combinations of previous days that can be evaluated in the logical query 810, which are Monday/Tuesday; Monday/Wednesday; and Tuesday/Wednesday. Here, combining any one of the combinations of previous days with the most recent BG does not result in three BG's falling within the three hour time bracket.

Note that in the embodiment set forth in Table 1, only one glucose concentration per day was depicted that exceeds the high threshold and flagged as fasting. In other situations, there may be more than one glucose concentration per day that exceed the high threshold and are flagged as fasting. In such a case, the number of combinations of 3 BG's that need to be evaluated by the logic 800 will increase.

As a further demonstration of the applicability of logic routine 800, consider that the user further conducted a most recent BG measurement on the Saturday following the Friday (of Table 1), set forth here in Table 2.

TABLE 2

| Monday-750 AM | Exceeds High Threshold |
| | Flagged as Fasting BG result |
| Tuesday-10:49 AM | Exceeds High Threshold |
| | Flagged as Before Meal BG result |
| Wednesday-7:40 AM | Exceeds High Threshold |
| | Flagged as Fasting BG result |
| Thursday-11:30 AM | Exceeds High Threshold |
| | Flagged as Before Meal BG result |
| Friday-9:00 AM | Exceeds High Threshold |
| | Flagged as Fasting BG result |
| Saturday-11:50 AM | Exceeds High Threshold |
| (Most Recent BG) | Flagged as Before Meal BG result |

In Table 2, the logic 800 would detect a high trend alert on Saturday (at 11:50 AM), which would be annunciated with the most recent BG. Note that there are six combinations of previous days that can be evaluated in the logical query 810, which are Monday/Tuesday; Monday/Wednesday; Monday/Thursday; Tuesday/Wednesday; Tuesday/Thursday; and Wednesday/Thursday. The 3 hour time bracket can include, in chronological order for time of day, 10:49 AM (Tuesday), 11:30 AM (Thursday), and 11:50 AM (Saturday), where the difference between the latest time and the earliest time is less than three hours (i.e., 11:50 AM minus 10:49 AM=1 hour and 1 minute). Thus, the Tuesday, Thursday, and Saturday BG's fall within the three hour time bracket. In summary based on Table 2, the user would be provided two messages: one on Friday and another message on Saturday. Alternatively, however, only one message may be generated on Saturday that reports the two high trends by prioritization of the trend data. Prioritization of the high trend or low trend reports can be based on the following: once a glucose value is used for a (high or low) trend, it will no longer be included in other (high/low) trends; if multiple trends are detected, the tightest clustering of results will be the one reported; or if there are multiple high and low BG measurements with an hour, only the first will be included in trend analysis (i.e., if there are either multiple high values with an hour or multiple low values within an hour, only the first will be included in trend analysis). Alternatively, the prioritization can be based on based on chronological closeness or based on the tightness of the clustering which can be determined by the closest 2 BG results in time to the most recent BG result, or the closest 3 BG results in time to the most recent BG result.

Although exemplary embodiments have been described in relation to a blood glucose meter, other diabetes management devices may also be utilized. For example, with reference to FIG. 8, analyte measurement and management unit 10 can be configured to wirelessly communicate with a handheld glucose-insulin data management unit or DMU such as, for example, an insulin pen 28, an insulin pump 48, a mobile phone 68, or through a combination of the exemplary handheld glucose-insulin data management unit devices in communication with a personal computer 26 or network server 70, as described herein. As used herein, the nomenclature "DMU" represents either individual unit 10, 28, 48, 68, separately or all of the handheld glucose-insulin data management units (28, 48, 68) usable together in a disease management system. Further, the analyte measurement and management unit or DMU 10 is intended to include a glucose meter, a meter, an analyte measurement device, an insulin delivery device or a combination of or an analyte testing and drug delivery device. In an embodiment, analyte measurement and management unit 10 may be connected to personal computer 26 with a cable. In an alternative, the DMU may be connected to the computer 26 or server 70 via a suitable wireless technology such as, for example, GSM, CDMA, BlueTooth, WiFi and the like.

Figure 8:
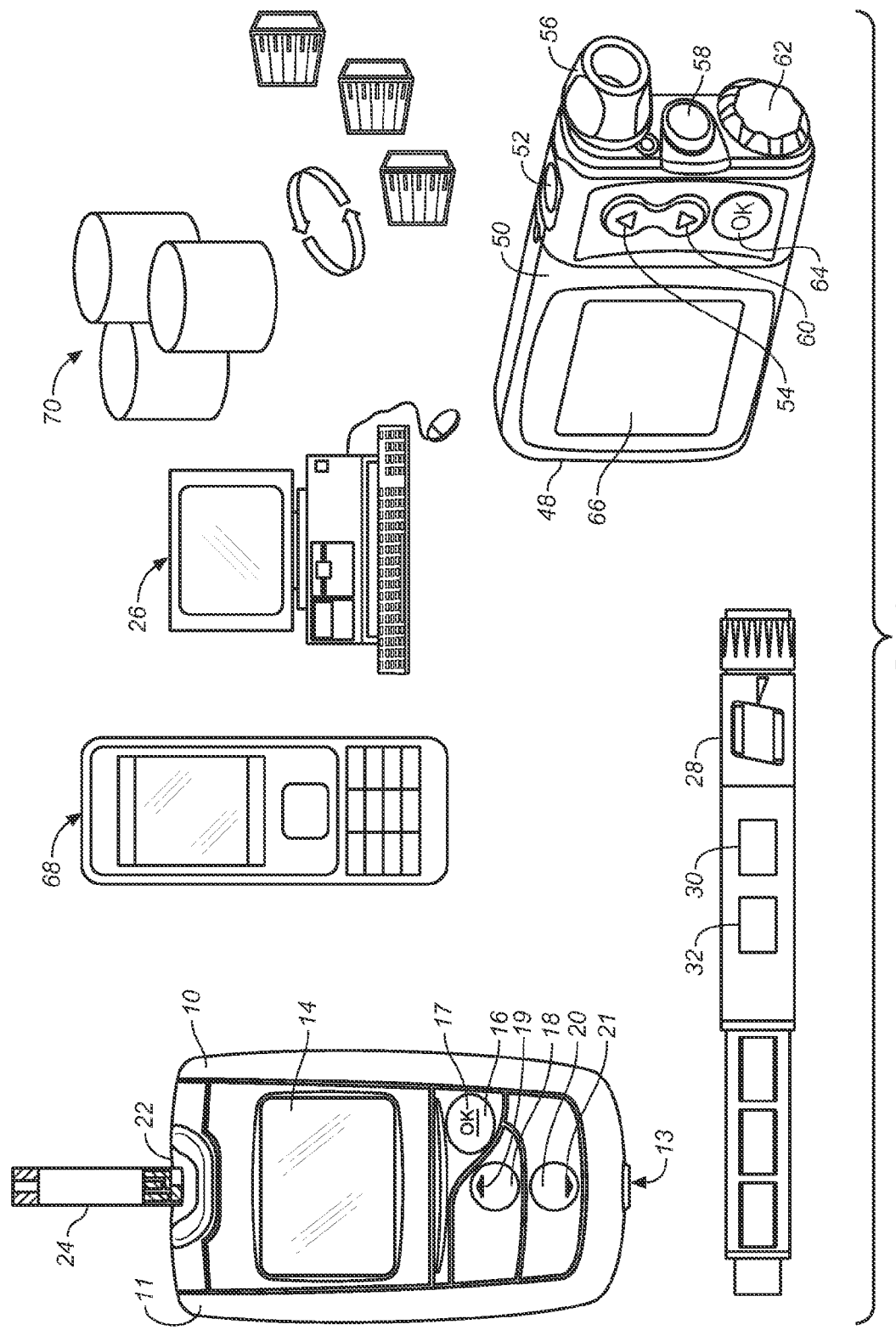
FIG. 8 illustrates various devices and systems in which the invention described and illustrated herein may be utilized.

Referring to FIG. 8, it should be noted that an insulin pen can be utilized to perform as described herein. Such insulin pen 28 may be provided with an electronic module 30 programmed to carry out the exemplary methods and variations thereof to assist user in management of diabetes. The device 28 may include a wireless module 32 disposed in the housing that, automatically without prompting from a user, transmits a signal to a wireless module 46 of the DMU 10. The wireless signal can include, in an exemplary embodiment, data to (a) type of therapeutic agent delivered; (b) amount of therapeutic agent delivered to the user; (c) time and date of therapeutic agent delivery; (d) trends of high or low BG results. A non-limiting example of such a user-activated therapeutic agent delivery device is described in co-pending U.S. Non-Provisional Application Nos. 12/407, 173; 12/417,875; and 12/540,217 , which is hereby incorporated in whole by reference with a copy attached hereto this application. Another non-limiting example of such a user-activated therapeutic agent delivery device is an insulin pen 28. Insulin pens can be loaded with a vial or cartridge of insulin, and can be attached to a disposable needle. Portions of the insulin pen can be reusable, or the insulin pen can be completely disposable. Insulin pens are commercially available from companies such as Novo Nordisk, Aventis, and Eli Lilly, and can be used with a variety of insulin, such as Novolog, Humalog, Levemir, and Lantus.

In yet a further alternative to the blood glucose meter 10, as shown in FIG. 8, a therapeutic dosing device can also be a pump 48 that includes a housing 50, a backlight button 52, an up button 54, a cartridge cap 56, a bolus button 58, a down button 60, a battery cap 62, an OK button 64, and a display 66. Pump 48 can be configured to dispense medication such as, for example, insulin for regulating glucose levels. As noted earlier, a microprocessor can be programmed to generally carry out the steps of various processes described herein. The microprocessor can be part of a particular device, such as, for example, a glucose meter, an insulin pen, an insulin pump, a server, a mobile phone, personal computer, or mobile hand held device.

Furthermore, the various methods described herein can be used to generate software codes using off-the-shelf software development tools such as, for example, Visual Studio 6.0, C or C++ (and its variants), Windows 2000 Server, and SQL Server 2000. The methods, however, may be transformed into other software languages depending on the requirements and the availability of new software languages for coding the methods. Additionally, the various methods described, once transformed into suitable software codes, may be embodied in any computer-readable storage medium that, when executed by a suitable microprocessor or computer, are operable to carry out the steps described in these methods along with any other necessary steps.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method of notifying a user of a high trend in blood glucose values obtained with a diabetes management unit having a microprocessor coupled to a display, memory and user interface, the method comprising:
   performing with the microprocessor, a plurality of blood glucose measurements of the user;
   storing in the memory, the plurality of blood glucose measurements of the user;
   determining, using the microprocessor, whether a most recent blood glucose measurement measured at a given time during a day is above a pre-determined high threshold;
   if the determining indicates that the most recent blood glucose measurement is above the pre-determined high threshold, then evaluating with the microprocessor whether the most recent blood glucose measurement is tagged as either being a measurement before a meal or a measurement made during a fasting period;
   if the evaluating indicates that the most recent blood glucose measurement is tagged as being either a measurement before a meal or a measurement made during a fasting period, then determining using the microprocessor whether there are two or more blood glucose measurements stored in memory over the previous N number of days that are above the pre-determined high threshold;
   if the determining indicates there are two or more blood glucose measurements stored in memory over the previous N number of days that are above the pre-determined high threshold, then determining using the microprocessor whether the two or more blood glucose measurements determined to exceed the pre-determined high threshold were tagged as being either being a measurement before a meal, a measurement made during a fasting period or both before a meal and during a fasting period;
   if the determining indicates the two or more blood glucose measurements determined to exceed the predetermined high threshold were tagged as being either being a measurement before a meal, a measurement made during a fasting period, or both during a meal and during a fasting period, then determining using the microprocessor whether the most recent blood glucose measurement and the two or more blood glucose measurements were performed within a time frame of approximately X hours that brackets the given time during each day but over prior days, wherein a difference in time between the most recent blood glucose measurement and an earliest blood glucose measurement taken over prior days is less than X hours; and upon achievement of the evaluating that the most recent blood glucose measurement and the two or more blood glucose measurements were performed within the time frame of approximately X hours that brackets the given time during each day but over prior days, then annunciating a high trend warning.

2. The method of claim 1, in which the prior N number of days comprises any number from about 2 to about 90.

3. The method of claim 1, in which the prior N number of days comprises any number from about 2 to about 5.

4. The method of claim 1, in which the prior N number of days is 4.

5. The method of claim 1, in which the X hours comprises any number between about 1 and about 7 hours.

6. The method of claim 1, in which the X hours comprises any number from about 1 to about 3 hours.

7. The method of claim 1, in which the predetermined high threshold comprises about 150 mg of glucose per deciliter of blood.

8. The method of claim 1, in which the annunciating comprises annunciating different message formats with generally the same meaning.

9. A diabetes management system comprising:
a glucose test strip; and
a diabetes management unit comprising:
 a housing including a test strip port configured to receive the glucose test strip;
 a user interface;
 a microprocessor coupled to the test strip port to provide data regarding an amount of glucose measured in a user's physiological fluid deposited on the test strip, the microprocessor further coupled to a memory, and user interface buttons;
 the microprocessor being programmed to:
  a) perform a plurality of blood glucose measurements of the user;
  b) store the plurality of blood glucose measurements of the user in the memory;
  c) determine whether a most recent blood glucose measurement measured at a given time during a day is above a predetermined high threshold;
  d) if a determination indicates that the most recent blood glucose measurement is above the predetermined high threshold, then determine whether the most recent blood glucose measurement is tagged as either being a measurement before a meal or a measurement made during a fasting period;
  e) if a determination indicates that the most recent blood glucose measurement is tagged as being a measurement before a meal or a measurement made during a fasting period, or both before a meal and during a fasting period, then determine whether there are two or more blood glucose measurements stored in memory over the previous N number of days that are above the predetermined high threshold;
  f) if a determination indicates there are two or more blood glucose measurements stored in memory over the previous N number of days that are above the predetermined high threshold, then determine whether the two or more blood glucose measurements determined to exceed the predetermined high threshold were tagged as being either being a measurement before a meal, a measurement made during a fasting period or both before a meal and during a fasting period;
  g) if a determination indicates the two or more blood glucose measurements determined to exceed the predetermined high threshold were tagged as being either being a measurement before a meal, a measurement made during a fasting period, or both before a meal and during a fasting period, then determine whether the most recent blood glucose measurement and the two or more blood glucose measurements were performed within a time frame of approximately X hours that brackets the given time during each day but over prior days, wherein a difference in time between the most recent blood glucose reading and an earliest blood glucose reading is less than X hours; and
  h) upon a determination that the most recent blood glucose measurement and the two or more blood glucose measurements were performed within the time frame of approximately X hours that brackets is higher than the high threshold, then annunciate a high trend warning.

10. The system of claim 9, in which the prior N number of days comprises any number from about 2 to about 90.

11. The system of claim 9, in which the prior N number of days comprises any number from about 2 to about 5.

12. The system of claim 9, in which the prior N number of days is 4.

13. The method of claim 9, in which the X hours comprises any number between about 1 and about 7 hours.

14. The method of claim 9, in which the X hours comprises any number from about 1 to about 3 hours.

15. The method of claim 9, in which the predetermined high threshold comprises about 150 mg of glucose per deciliter of blood.

16. The system of claim 9, in which the microprocessor is programmed to annunciate different message formats with generally the same meaning.

* * * * *